United States Patent
Zimmermann et al.

(10) Patent No.: US 9,739,794 B2
(45) Date of Patent: Aug. 22, 2017

(54) SAMPLE INJECTOR WITH DISCONNECTABLE INJECTION NEEDLE

(75) Inventors: Hans-Peter Zimmermann, Waldbronn (DE); David Jenaro, Nufringen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 578 days.

(21) Appl. No.: 14/124,908

(22) PCT Filed: Jun. 9, 2011

(86) PCT No.: PCT/EP2011/059644
§ 371 (c)(1),
(2), (4) Date: Dec. 9, 2013

(87) PCT Pub. No.: WO2012/167832
PCT Pub. Date: Dec. 13, 2012

(65) Prior Publication Data
US 2014/0116159 A1  May 1, 2014

(51) Int. Cl.
*G01N 35/10* (2006.01)
*G01N 30/16* (2006.01)
(Continued)

(52) U.S. Cl.
CPC ............ *G01N 35/10* (2013.01); *B01L 3/0241* (2013.01); *B01L 3/0279* (2013.01); *G01N 30/16* (2013.01);
(Continued)

(58) Field of Classification Search
CPC . G01N 35/10; G01N 2035/1051; G01N 30/24
See application file for complete search history.

(56) References Cited

U.S. PATENT DOCUMENTS 4,974,458 A  12/1990  Koike
4,982,597 A   1/1991  Berger
(Continued)

FOREIGN PATENT DOCUMENTS

CN   101925822 A   12/2010
DE   102007000622   5/2008
(Continued)

OTHER PUBLICATIONS

Drexler, et al. "Improvements to the Sample Manipulation Design of a LEAP CTC HTS PAL Autosampler Used for High-Throughput Qualitative and Quantitative Liquid Chromatography-Mass Spectrometry Assays", Journal of the Association for Laboratory Automation, Elsevier, vol. 12, No. 3 XP022078345 ISSN: 1535-5535, DOI: 10.1016/J.JALA.2007.01.002 p. 154, right-hand column; figure 3b p. 154, left-hand column.
(Continued)

*Primary Examiner* — Paul West

(57) ABSTRACT

A sample injector for injecting a fluid into a fluidic path, wherein the sample injector comprises a robot arm configured for moving an injection needle, when being connected to the robot arm, between a fluid container containing the fluid and a seat in fluid communication with the fluidic path, the needle configured for aspirating the fluid from the fluid container, when the needle has been moved to the fluid container, and for injecting aspirated fluid into the fluidic path, when the needle is accommodated in the seat, and the seat configured for accommodating the needle and providing fluid communication with the fluidic path, wherein the robot arm is configured for selectively disconnecting the needle from the robot arm when the needle is accommodated in the seat, and wherein the robot arm is configured for performing a further task while the needle is disconnected from the robot arm.

48 Claims, 21 Drawing Sheets

(51) Int. Cl.
  *G01N 30/18* (2006.01)
  *G01N 30/24* (2006.01)
  *B01L 3/02* (2006.01)

(52) U.S. Cl.
  CPC ............ *G01N 30/18* (2013.01); *G01N 30/24* (2013.01); *G01N 35/109* (2013.01); *B01L 2200/0631* (2013.01); *B01L 2200/0647* (2013.01); *B01L 2200/0689* (2013.01); *B01L 2300/022* (2013.01); *B01L 2300/044* (2013.01); *B01L 2300/0672* (2013.01); *B01L 2300/0681* (2013.01); *B01L 2300/0829* (2013.01); *B01L 2300/0838* (2013.01); *B01L 2400/0406* (2013.01); *G01N 2030/185* (2013.01); *G01N 2035/103* (2013.01)

(56) References Cited

U.S. PATENT DOCUMENTS

| | | | |
|---|---|---|---|
| 5,305,650 | A | 4/1994 | Koike et al. |
| 7,138,050 | B2 | 11/2006 | Maruyama et al. |
| 7,555,937 | B2 | 7/2009 | Hirayama et al. |
| 7,635,326 | B2 | 12/2009 | Gueller et al. |
| 2006/0259195 | A1* | 11/2006 | Eliuk ................ A61J 1/20 700/245 |
| 2007/0095158 | A1 | 5/2007 | Maeda |
| 2010/0037919 | A1 | 2/2010 | Doebelin et al. |
| 2011/0120237 | A1* | 5/2011 | Leroi ................ G01N 35/1079 73/863.83 |

FOREIGN PATENT DOCUMENTS

| | | |
|---|---|---|
| DE | 102008041863 | 4/2009 |
| DE | 102008041863 A1 | 4/2009 |
| EP | 309596 | 4/1989 |
| EP | 0990899 | 4/2000 |
| EP | 1366822 | 3/2003 |
| EP | 1577004 | 9/2005 |
| EP | 2166361 A2 | 3/2010 |

OTHER PUBLICATIONS

Invitation to Pay Additional Fees and Partial Search Report mailed Mar. 2, 2012 in International Patent Application No. PCT/EP2011/059644.

International Search Report and Written Opinion mailed May 10, 2012 in International Patent Application No. PCT/EP2011/059644.

Machine translation of DE102008041863A1, published Apr. 9, 2009.

Machine translation of EP2166361, published Mar. 24, 2010.

Office Action mailed Jul. 14, 2015 in Chinese Application No. 201180071530.X (Unofficial/Non-certified translation provided by foreign agent included).

Non-Final Office action dated Dec. 1, 2016 from related U.S. Appl. No. 14/264,755.

Notice of Decision to Grant Received dated May 4, 2017 from related Chinese Application No. 201180071530.X.

* cited by examiner

SAMPLE INJECTOR WITH DISCONNECTABLE INJECTION NEEDLE

The present application is a National Stage application under 35 U.S.C. §365 of International Patent Application No. PCT/EP2011/059644 filed on Jun. 9, 2011 naming Hans-Peter Zimmerman, et al. as inventors. Priority is claimed from International Patent Application No. PCT/EP2011/059644 and the entire disclosure of International Patent Application No. PCT/EP2011/059644 is specifically incorporated herein by reference.

BACKGROUND ART

The present invention relates to a sample injector for a sample separation system, in particular for high performance liquid chromatography applications.

In liquid chromatography, a fluidic sample and an eluent (liquid mobile phase) may be pumped through conduits and a column in which separation of sample components takes place. In a sample loop, the sample may be injected into a fluidic path by a mechanically drivable needle. The drivable needle is controllable to be moved out of a seat of the sample loop into a vial or any other fluid container to receive a fluid and back from the vial into the seat. The column may comprise a material which is capable of separating different components of the fluidic analyte. Such a material, so-called beads which may comprise silica gel, may be filled into a column tube which may be connected downstream to other components, such as a detector, a fractioner, a waste, etc., by conduits.

U.S. Pat. No. 7,555,937 discloses a sample injection device, a sample injection method, and a liquid chromatograph that control the flow of a mobile phase using a switching valve. The sample injection device includes a port connected to a separation column, a pump for supplying a mobile phase, first and second sample injection needles, a syringe, and a valve configured to selectively connect the first sample injection needle to the pump or the syringe and to connect the second sample injection needle to the pump. When the first sample injection needle is attached to the port, the first sample injection needle is connected to the pump through operation of the valve. When the second sample injection needle is attached to the port, the first sample injection needle is connected to the syringe and the second sample injection needle is connected to the pump.

U.S. Pat. No. 7,635,326 discloses a tool holder which can be displaced in an x-direction, in a y-direction that is perpendicular thereto, and in a z-direction that is perpendicular to both the x-direction and the y-direction, and which can rotate about the z-direction. A solid matter dosing head, provided as a tool, is automatically attached in a removable manner to the tool holder by means of a permanent magnet. The tool can be easily exchanged for another tool due to this automatic removable attachment of said tool to the tool holder involving the use of a permanent magnet.

DE 102007000622, EP 1,366,822, and U.S. Pat. No. 7,138,050 disclose further fluid handling systems.

The product G1367 of the applicant Agilent Technologies is an example for a commercially available needle assay well plate autosampler.

However, fluid handling and proper operation of movable parts in a sample separation device may still be a challenge.

DISCLOSURE

It is an object of the invention to enable efficient fluid handling in a sample separation system.

According to an exemplary embodiment of a first aspect, a sample injector for injecting a fluid into a fluidic path is provided, wherein the sample injector comprises a robot arm configured for moving an injection needle, when being connected to the robot arm, between a fluid container containing the fluid and a seat in fluid communication with the fluidic path, the injection needle configured for aspirating the fluid from the fluid container, when the injection needle has been moved to the fluid container, and for injecting aspirated fluid into the fluidic path, when the injection needle is accommodated in the seat, and the seat configured for accommodating the injection needle and providing fluid communication with the fluidic path, wherein the robot arm is configured for selectively disconnecting the injection needle from the robot arm when the injection needle is accommodated in the seat, and wherein the robot arm is configured for performing a further task while the injection needle is disconnected from the robot arm.

According to another exemplary embodiment of the first aspect, a method of injecting a fluid into a fluidic path is provided, wherein the method comprises moving an injection needle connected to a robot arm to a fluid container for aspirating the fluid in the injection needle, moving the injection needle connected to the robot arm to a seat in fluid communication with the fluidic path, disconnecting the injection needle from the robot arm when the injection needle is accommodated in the seat, injecting the aspirated fluid from the injection needle into the fluidic path when the injection needle is accommodated in the seat, and performing a further task by the robot arm while the injection needle is disconnected from the robot arm.

According to an exemplary embodiment of a second aspect, a sample injector for injecting a fluid into a fluidic path is provided, wherein the sample injector comprises a robot arm configured for taking out a selected one of a plurality of fluid containers, each containing a fluid, from a fluid container rack and placing the selected fluid container on a fluid container support, wherein the robot arm is further configured for moving an injection needle between the selected fluid container placed on the fluid container support containing the fluid and a seat in fluid communication with the fluidic path, and the injection needle configured for aspirating the fluid from the fluid container, when the injection needle has been moved to the fluid container, and for injecting aspirated fluid into the fluidic path, when the injection needle is accommodated in the seat.

According to another exemplary embodiment of the second aspect, a method of injecting a fluid into a fluidic path is provided, wherein the method comprises taking out a selected one of a plurality of fluid containers, each containing a fluid, from a fluid container rack and placing the selected fluid container on a fluid container support by a robot arm, aspirating the fluid from the selected fluid container placed on the fluid container support by an injection needle supported by the robot arm, moving the injection needle to a seat in fluid communication with the fluidic path by the robot arm, and injecting the aspirated fluid into the fluidic path when the injection needle is accommodated in the seat.

According to an exemplary embodiment of a third aspect, a sample injector for injecting a fluid into a fluidic path is provided, wherein the sample injector comprises a robot arm configured for handling a plurality of fluid containers, each containing a fluid, and an injection needle, configured for aspirating the fluid from one of the plurality of fluid containers and for injecting the aspirated fluid into the fluidic path, wherein the robot arm has a first lift mechanism configured for handling the plurality of fluid containers over a first stroke length along a lift axis, wherein the robot arm has a second lift mechanism configured for handling the injection needle over a second stroke length along the lift axis, and wherein the first stroke length differs from the second stroke length.

According to another exemplary embodiment of the third aspect, a method of injecting a fluid into a fluidic path is provided, wherein the method comprises handling a selected one of a plurality of fluid containers, each containing a fluid, by actuating a first lift mechanism of a robot arm operable over a first stroke length along a lift axis, and handling an injection needle, for aspirating the fluid from one of the plurality of fluid containers and for injecting the aspirated fluid into the fluidic path, by actuating a second lift mechanism of the robot arm operable over a second stroke length along the lift axis, wherein the first stroke length differs from the second stroke length.

According to still another exemplary embodiment (which can be combined with any of the first to third aspects), a fluid separation system for separating compounds of a fluid in a mobile phase is provided, wherein the fluid separation system comprises a mobile phase drive, preferably a pumping system, configured to drive the mobile phase through the fluid separation system, a separation unit, preferably a chromatographic column, configured for separating compounds of the fluid in the mobile phase, and a sample injector having the above mentioned features and being configured for injecting the fluid in the fluidic path between the mobile phase drive and the separation unit.

According to an embodiment of the first aspect, an injection needle may be temporarily disconnected from a robot arm in a parking position while fluid which has previously been aspirated into the injection needle can be injected into a fluidic path coupled with a conduit of the seat. Thus, in the time interval in which the fluid may be further processed from the injection needle placed in a corresponding needle seat to the connected fluidic path and further downstream, the needle disconnection allows the robot to freely perform other tasks which render the management of the robot resources more efficiently. According to this first aspect, the injection of the aspirated fluid from the injection needle via the seat into the fluidic path (particularly a high pressure path between a mobile phase drive unit and a separation unit of a chromatography system) may be performed after having disconnected the injection needle from the robot arm. Hence, after this mechanical and fluidic decoupling of the injection needle from the robot arm, i.e. while the robot arm can perform any other task, the injection needle may rest with one end pressure-tightly connected to the seat and with the other end unconnected but preferably sealed with regard to an environment. Thus, in this operation state, the fluid can be transferred from the disconnected and sealed injection needle through the seat and to the fluidic path, while simultaneously the free capacity of the robot arm may be used for the mentioned other tasks to render operation of the system highly efficiently and the fluid handling very fast.

According to an embodiment of the second aspect, a robot arm can be configured to provide at least two functions, i.e. the handling of fluid containers which may be stored in a fluid container rack, and the handling of an injection needle for aspirating fluid from a fluid container selected out of fluid container rack for later moving the fluid-loaded needle to the seat in order to inject the aspirated fluid into the fluidic path related to this seat. Therefore, one and the same robot may be used very efficiently for two different tasks which usually cannot be performed at the same time, so that a compact system is provided in which a robot can be efficiently used.

According to an embodiment of the third aspect, a robot is provided which comprises two separately operable lift mechanisms with regard to one and the same lifting direction so that different lifting performances can be performed with different stroke heights (i.e. with different distances between an upper and a lower reversal position) using the first and the second lift mechanism. For instance, a larger stroke length and corresponding larger lift mechanism may be needed for handling a plurality of fluid containers accommodated in a fluid container rack vertically stacked above one another. For this task, the robot needs to move over the entire height of the arrangement of the fluid containers. However, for handling an injection needle, a smaller stroke length and correspondingly a smaller lift mechanism may be sufficient, since the needle needs to be lifted only over a smaller range in this scenario.

In the following, further embodiments of any of the above sample injectors (i.e. of any of the above first to third aspects) will be explained. However, these embodiments also apply to any of the above methods (i.e. to any of the above first to third aspects) and to the fluid separation system.

In an embodiment, the robot arm is configured for performing a fluid handling task while the injection needle is disconnected from the robot arm. Thus, an injection task and a fluid handling task may be performed in parallel which renders the operation of the system more efficiently.

In an embodiment, the robot arm is configured for handling at least one selected of a plurality of fluid containers, each containing a fluid, from a fluid container rack while the injection needle is disconnected from the robot arm. Therefore, the robot may have a provision which enables to robot to perform both tasks, i.e. handling a needle and handling a fluid container such as a vial or a well plate.

In an embodiment, the robot arm is configured for being moved, particularly for moving another body along, while the injection needle is disconnected from the robot arm. Such a moving may be a spatial displacement in one, two or three dimensions and allows the robot arm to perform a moving task such as the moving of a connected member like a fluid container while the needle remains disconnected in the seat.

In an embodiment, the robot arm is configured for, while the injection needle is disconnected from the robot arm, serving another injection needle. Therefore, it is not only possible that the robot arm, while the injection needle is disconnected, handles fluid containers, but it is additionally or alternatively possible that a parallel handling of multiple injection needles is performed with one and the same robot arm. Therefore, it is for instance possible in the context of a chromatographic separation, to separate fluidic samples in different fluidic paths simultaneously.

In an embodiment, the robot arm is configured for performing the further task under control of a software program. Therefore, a sequence of automatically performed operation steps can be carried out by a software controlling the robot arm which can further increase the efficiency of the robot resources. Any of the above-described and below-described tasks may be controlled by software.

In an embodiment, the injection needle and the seat are configured to cooperate so that the injection needle is accommodated in the seat in a fluid-tight manner, particularly in a pressure-tight manner. For instance, placing the needle in the seat may activate a mechanism in a self-acting manner which sealingly presses the needle into the seat. This can be advantageous in a chromatographic application in which a pump injects a fluid into a fluidic path at a relatively high pressure. Thus, by configuring the connection between needle and seat pressure-tight, it is possible to perform the injection without a leak and hence without a loss of fluidic sample.

In an embodiment, the sample injector comprises a needle park station configured for retaining the injection needle when the injection needle is accommodated in the seat. Such a needle park station may be a member which is capable of holding the injection needle in the disconnected state and which may also manage, for instance by a mechanical mechanism, the handover or transfer of the needle between robot arm and seat.

In an embodiment, the robot arm and/or the injection needle and/or the seat and/or the needle park station is configured to cooperate for sealing an internal fluid conduit of the injection needle with regard to an environment upon disconnecting the injection needle from the robot arm. Thus, in this advantageous embodiment, it is possible that an upper end of the capillary of the injection needle is sealed with regard to the environment (excluding the seat) making it possible to inject the fluid previously aspired by the injection needle into a connected fluidic conduit of the seat.

In an embodiment, the robot arm and/or the injection needle and/or the seat and/or the needle park station is configured so that, upon inserting the injection needle into the seat by the robot arm, a biasing element (such as a spring, for instance a helical spring), particularly of the injection needle or of the seat, is biased so as to exert a sealing force between the injection needle and the seat, and a mutual locking mechanism of the injection needle and the needle park station is activated. Such a biasing element may be a spring which presses the injection needle against the seat with a certain spring force, thereby supporting or promoting a fluid-tight connection. Moreover, it can then be ensured that the needle is safely stored in the needle park station by simultaneously activating the locking mechanism. Such a locking mechanism may be activated by the engagement of two cooperating engagement elements.

In an embodiment, the robot arm and the injection needle comprise cooperating first retaining elements configured for retaining the injection needle at the robot arm with a first retaining force being operative while the injection needle is outside the seat. The needle park station and the injection needle may comprise cooperating second retaining elements configured for retaining the injection needle at the needle park station with a second retaining force being larger than the first retaining force and being operative when the injection needle is inserted into the seat so that subsequently retracting the robot arm from the seat releases the injection needle from the robot arm and retains the injection needle at the needle park station. By this mechanism of two retaining systems having different retaining forces, it is possible to disconnect the injection needle merely by inserting it into a needle park station and by pulling the robot arm upwardly afterwards. Consequently, the stronger retaining force between needle park station and needle will then force the needle to remain at the needle park station and being in fluid communication with the fluid conduit of the seat.

In an embodiment, the robot arm and the injection needle comprise cooperating retaining elements configured for retaining the injection needle at the robot arm. The robot arm is configured for lowering the injection needle in a lowering direction (particularly in a vertical direction) to place the injection needle in the needle park station and for subsequently performing a motion in a lateral direction (particularly in a horizontal direction) angled relative to the lowering direction to disengage the cooperating retaining elements, thereby disconnecting the injection needle from the robot arm. Hence, the robot arm decouples the needle by a sideward motion and thereby remains in the needle park station.

In an embodiment, the mutual locking mechanism is provided by the second retaining elements. Thus, the second retaining elements do not only result in a disconnection of the needle but may also ensure the mutual locking which renders the device simple and compact and nevertheless reliable in the needle transfer operation.

In an embodiment, the needle park station comprises a latch being actuable by the robot arm to disengage the second retaining elements from one another so that subsequently retracting the robot arm pulls the injection needle along with the robot arm. Therefore, the robot arm may actuate the latch so as to release the connection between the disconnected needle and the needle park station, thereby again connecting the needle to the robot arm by the first retaining elements.

In an embodiment, the injection needle has a lever mechanism operable by the robot arm for reducing a force to be provided by the robot arm required for sealing the fluid conduit by lever action. By such a lever mechanism, it is possible to operate the robot arm with reduced requirements with regard to its force exertion, since a force transfer mechanism may allow actuation with a lower force over a larger actuation length. For this purpose, a leverage effect may be used.

In an embodiment, the robot arm and/or the injection needle and/or the seat is configured to cooperate so that, upon inserting the injection needle into the seat, a locking mechanism is activated for locking the injection needle to the seat and an unlocking mechanism is simultaneously activated for unlocking the injection needle from the robot arm. Thus, two mechanisms may be actuated at the same time or by a single motion of the robot arm, one being activated and the other one being deactivated.

In an embodiment, the locking mechanism and/or the unlocking mechanism is or are configured as a mechanical latching mechanism, a mechanical clamping mechanism and/or a magnetic mechanism. However, other mechanisms such as an electric mechanism or the like may be possible as well.

In an embodiment, the sample injector comprises at least one further seat in fluid communication with at least one further fluidic path, wherein the robot arm is configured for accommodating the injection needle selectively in the seat or in at least one of the at least one further seat. In such an embodiment, the fluidic device may have a plurality of different seats each being capable of receiving a respective needle. This allows to serve multiple seats and hence multiple connected fluid separation systems with the same robot arm.

In an embodiment, the sample injector comprises at least one further needle park station assigned to the at least one further seat and configured for retaining the injection needle when the injection needle is accommodated in a corresponding one of the at least one further seat. Therefore, for each of a plurality of seats, an assigned one of the plurality of needle park stations may be foreseen so that the disconnection of the corresponding needles can be managed by a separate needle park station in each seat. This may allow to further parallelize operation.

In an embodiment, the sample injector comprises at least one further injection needle movable by the robot arm, when being connected thereto, between the fluid container containing the fluid and selectively the seat or one of the at least one further seat. Therefore, also a plurality of injection needles may be implemented so that a highly modular system of multiple injection needles, multiple needle park stations and multiple seats can be implemented. The different seats/needle park stations/needles may be identical or may differ with regard to at least one parameter, for instance may differ in size.

In an embodiment, the robot arm is configured for mounting at least one further tool additionally or alternatively to the injection needle. The at least one further tool may comprise a gripper configured for gripping a vial (or any other fluid container such as a well plate), a reader configured for reading an identification feature of the fluid container or a vial (for instance using a wireless reader technology implementing an RFID tag), a filter for filtering the fluid, a pipette tip, a mixer for mixing the fluid, a punching tool for punching a septum covering a fluid container, and a plate handling tool configured for handling plates having multiple fluid receptacles (such as a well plate). However, other tools are possible as well. The robot arm may therefore be capable of providing more than one task at the same time including needle handling, fluid container handling and at least one additional capability. Therefore, a multiple purpose robot arm may be provided. The gripper may also be configured for gripping SPE (solid phase extraction) cartridges. An SPE is a tube filled with packing material on which sample from a previous processing step can be purified and concentrated. The robot can grip such cartridges and place the cartridge in a special needle park station for sealing it (similar to the sealing of the needle to the hydraulic system). Now the sample can be released from the packing material and can be injected into a liquid chromatography system.

In an embodiment, the robot arm comprises a stripper tool configured for stripping off a fluid container from the injection needle after having aspirated the fluid from the fluid container. Such a stripper tool may allow to apply a force for separating a needle and a fluid container such as a vial from one another. When aspirating a fluid in a vial or other fluid container, it may be necessary that the needle penetrates through a membrane covering the vial. Such a membrane may ensure a sterile storage of the sample in the vial. However, after having penetrated this membrane, it may happen that there remains a connection force between needle and membrane. The robot-bound stripper tool also to release such an undesired connection.

In an embodiment, the robot arm carries a capillary being in fluid communication with a fluid conduit of the injection needle when the injection needle is accommodated in the seat. Such a capillary may be in fluid communication with a metering device of the sample injector, the metering device defining an amount of fluid to be aspirated into the needle.

In an embodiment, the robot arm is configured for taking out a selected one of a plurality of fluid containers, each containing a fluid, from a fluid container rack and placing the selected fluid container on a fluid container support, wherein the robot arm is further configured for moving the injection needle between the selected fluid container placed on the fluid container support containing the fluid and the seat. For example, the fluid containers may be well plates or the like which can be arranged or stacked vertically (and/or horizontally) above one another in the fluid container rack which may be also be denoted as a well plate hotel. Apart from the needle handling task, the robot arm may also be able to handle each individual of the fluid containers, i.e. take a selected one out from the fluid container rack and place it on a support at a defined position.

In an embodiment, the robot arm has a first lift mechanism configured for handling a plurality of fluid containers, particularly when being vertically stacked in a fluid container rack, over a first stroke length along a lift axis, wherein the robot arm has a second lift mechanism configured for handling the injection needle over a second stroke length along the lift axis, wherein the first stroke length differs from, particularly is larger than, the second stroke length. Thus, particularly along a vertical axis, the robot arm may have two separate lift mechanisms (for instance two independently operable raise and lowering equipments) each of which allowing a handling over a certain stroke width which needs to be larger in many cases for handling vertically stacked fluid container racks as compared to a stroke width required for aspirating fluid into an injection needle and injecting this fluid into a fluidic conduit in the seat.

In an embodiment, the fluid container rack comprises a plurality of vertically stacked compartments each configured for accommodating a respective one of the plurality of fluid containers (such as well plates). Each compartment may be capable of receiving a well plate, for instance having 96 or any other plurality of wells with fluidic samples in it. It is also possible that individual vials or groups of vials are stored in the compartments.

In an embodiment, the fluid container rack is operable with a push loading drawer mechanism. Such a mechanism may be actuated by the robot arm for taking fluid containers out of the fluid container rack or for inserting fluid containers into the fluid container rack.

In an embodiment, the robot arm is configured for taking a fluid container from the fluid container support and for moving this fluid container into the fluid container rack. For this purpose, the robot arm may be configured with a certain gripper for gripping fluid containers.

In an embodiment, at least a part of the plurality of fluid containers is a sample plate comprising a plurality of receptacles each configured for accommodating a fluid. Such a sample plate may be a well plate or microtiter plate. A microtiter plate is a flat plate with multiple wells used as small test tubes. The microplate has become a standard tool in analytical research and clinical diagnostic testing laboratories.

In an embodiment, the robot arm is configured so that the injection needle is disconnectably mountable on the robot arm and a provision for handling a fluid container of the robot arm is disconnectably mountable or permanently mounted on the robot arm. Therefore, the robot arm may connect or disconnect with an injection needle and/or a fluid container on demand.

In an embodiment, the sample injector comprises only a single (i.e. exactly one) fluid container support configured for receiving exactly one fluid container, particularly exactly one well plate. Therefore, one specific position for receiving fluid containers from the fluid container rack may be defined. The robot arm will then place any (and only one at a time) fluid container taken from the fluid container rack onto this position so that it is very easy and only involves short moving paths for a needle for moving between a selected fluid container placed on the fluid container support on the one hand and a seat on the other hand. This renders operation of the device very efficient.

In an embodiment, the robot arm is configured for alternatingly handling the plurality of fluid containers and the injection needle. Thus, in a first operation mode, a fluid which has already been aspirated into the needle, the needle being already inserted into a seat, is injected into the fluidic path while the robot arm operates the fluid containers. In another operation mode, the needle is connected to the robot arm and aspirates fluid from a fluid container which has previously been mounted on the fluid container support. This allows to partially parallelize the tasks of fluid injection and fluid aspiration.

In an embodiment, the robot arm is configured for selectively disconnecting the injection needle from the robot arm when the injection needle is accommodated in the seat, wherein the robot arm is configured for handling at least one of the plurality of fluid containers of the fluid container rack while the injection needle is disconnected from the robot arm. This allows to efficiently use the resources of the robot arm.

In an embodiment, the robot arm is movable by a horizontal drive mechanism in a plane perpendicular to the lift axis. Therefore, apart from the lift direction, also movement along one or even two perpendicular horizontal directions is possible.

In an embodiment, the lift axis is a vertical axis. The vertical axis may be defined to be parallel to the direction of gravity force.

In an embodiment, the first lift mechanism and the second lift mechanism are operable independently from one another. This has the advantage that only one lift mechanism which is needed presently needs to be operated, whereas the other lift mechanism which is presently not required can be kept fixed.

A processing element may be filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The processing element may be a chromatographic column for separating components of the fluidic sample. Therefore, exemplary embodiments may be particularly implemented in the context of a liquid chromatography apparatus.

The sample separation device may be configured to conduct a liquid mobile phase through the processing element and optionally a further processing element. As an alternative to a liquid mobile phase, a gaseous mobile phase or a mobile phase including solid particles may be processed using the fluidic device. Also materials being mixtures of different phases (solid, liquid, gaseous) may be processed using exemplary embodiments. The sample separation device may be configured to conduct the mobile phase through the system with a high pressure, particularly of at least 600 bar, more particularly of at least 1200 bar.

The sample separation device may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector module of a liquid chromatography apparatus which sample injector module may take up a sample from a fluid container and may inject such a sample in a conduit for supply to a separation column. During this procedure, the sample may be compressed from, for instance, normal pressure to a higher pressure of, for instance several hundred bars or even 1000 bar and more. An autosampler may automatically inject a sample from the vial into a sample loop. A tip or needle of the autosampler may dip into a fluid container, may suck fluid into the capillary and may then drive back into a seat of a sample loop to then, for instance via a switchable fluidic valve, inject the fluid towards a sample separation section of the liquid chromatography apparatus. The sample in the sample loop may be a steel capillary or the like.

The sample separation device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The sample separation device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid Chromatography (HPLC) device by which different fractions of an analyte may be separated, examined and analyzed.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase.

Embodiments of the present invention might be embodied based on most conventionally available HPLC systems, such as the Agilent 1290 Series Infinity system, Agilent 1200

Series Rapid Resolution LC system, or the Agilent 1100 HPLC series (all provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable. One embodiment comprises two pumping apparatuses coupled either in a serial (e.g. as disclosed in EP 309596 A1) or parallel manner.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs. The illustration in the drawing is schematic.

Figure 1:
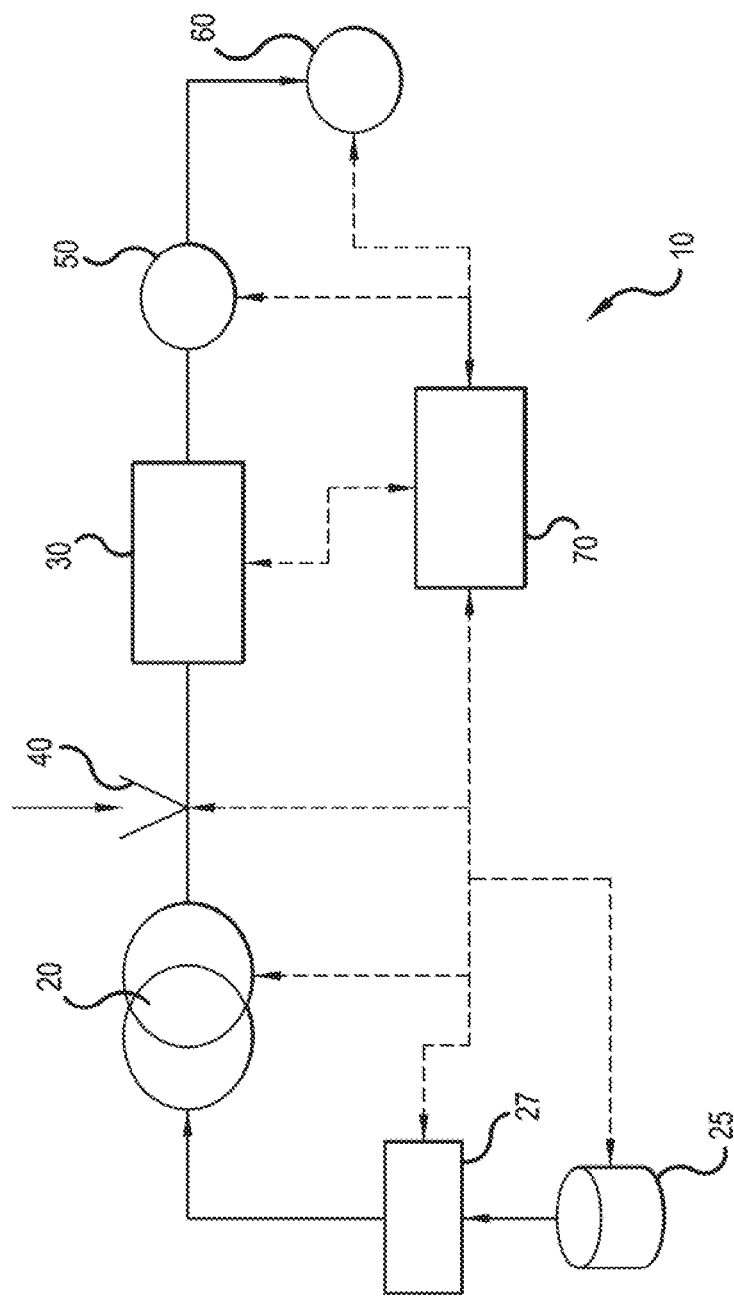
FIG. 1 shows a liquid separation device, in accordance with embodiments of the present invention, e.g. used in high performance liquid chromatography (HPLC).

The illustration in the drawing is schematic.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (having a needle/seat arrangement depicted in FIG. 1 schematically) is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). A switchable valve (not shown) can be operated so as to adjust a desired fluidic coupling within the liquid separation system 10. The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

In the following, referring to FIG. 2, a sample injector for use in a fluid separation system 10 as described in FIG. 1 for separating components of a fluidic sample in a mobile phase according to an exemplary embodiment of the invention will be explained.

The sample injector comprises a switchable valve 90, a sample loop 230 in fluid communication with the valve 90 and contributing to aspirating the fluidic sample from a vial 214 (or any other fluid container), and a metering pump 270 in fluid communication with the sample loop 230 and configured for introducing a metered amount of the fluidic sample into needle 202.

The switchable valve 90 comprises two valve members which are rotatable with respect to one another. By rotating these two valve members along a rotation axis which is perpendicular to the paper plane of FIG. 2, a plurality of ports 262 formed in one of the valve members and a plurality of oblong arcuate grooves 264 formed in the other one of the valve members can be selectively brought in or out of fluid communication with one another. Since the various ports 262 are connected to dedicated ones of fluidic channels of the fluidic system as shown in FIG. 2, automatically switching the valve 90 may allow to operate the fluidic system 10 in different fluid communication configurations. The valve 90 is configured as a six port high pressure valve in the embodiment of FIG. 2.

Fluid communication between the high pressure pump 20 and the separation column 30 can be accomplished by an according switching state of the valve 90. In such a fluidic path, a high pressure of for instance 100 MPa may be present which may be generated by the high pressure pump 20. In contrast to this, the pressure state in the sample loop 230 may be for instance smaller than 0.1 MPa when introducing a sample into the sample loop 230. When this sample loaded on sample loop 230 is to be loaded on column 30, the pressure in sample loop 230 is also high, for instance 100 MPa.

For the purpose of loading the sample, a needle 202 may be driven out of a correspondingly shaped seat 200 so that the needle 202 can be immersed into vial 214 accommodating a fluidic sample to be loaded onto the needle 202.

Figure 2:
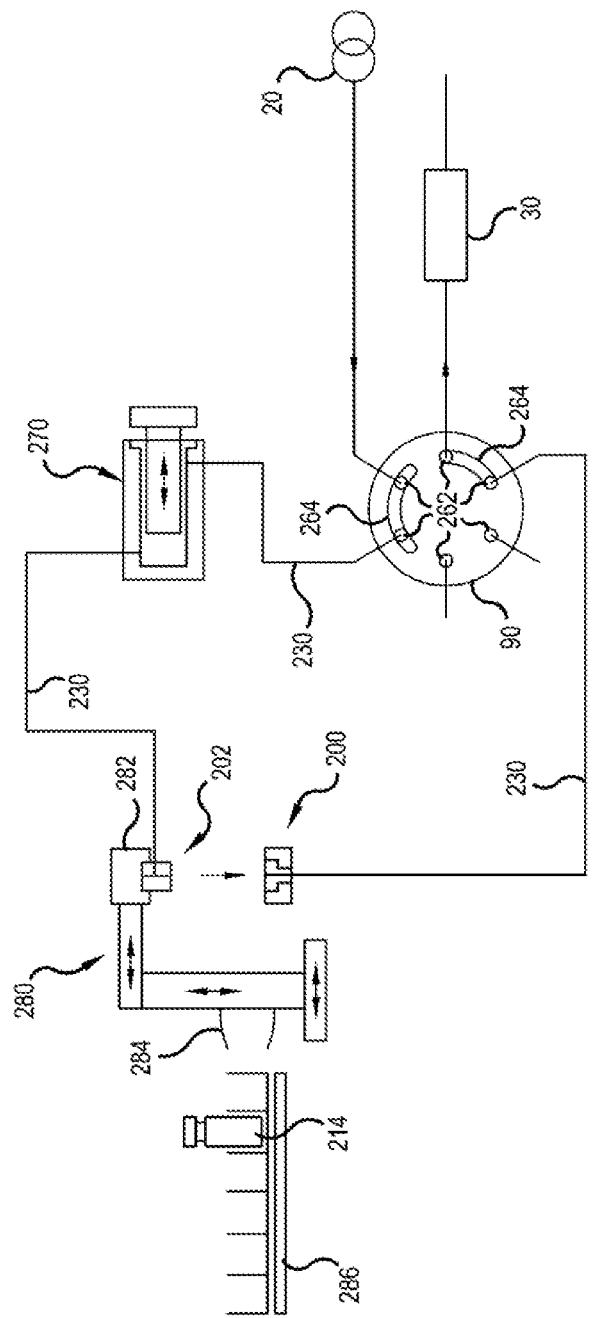
FIG. 2 to FIG. 4 show a sample injector of a liquid separation device in accordance with embodiments of the present invention in three different operation modes.

Hence, FIG. 2 shows the movable needle 202 which can be moved under control of a control unit (not shown, for instance a central processing unit or microprocessor), between vial 214 and seat 200.

Hence, when the needle body with its conically tapering tip is immersed into the vial 214, it is possible to suck a fluidic sample accommodated within vial 214 into the fluidic conduit in the needle body as well as into fluid connected conduits.

Subsequently, the sample may be loaded onto the column 30. However, for this purpose, it is required that the needle 202 be inserted into the seat 200. As can be taken from the schematic drawing in FIG. 2, also the seat 200 has a central bore which allows for fluid communication between the fluidic conduit of the needle 202 and the fluidic conduit of the seat 200. Therefore, the sample which has been previously loaded via the conduit of the needle body 204 can be conducted through the conduits and finally onto the column 30.

Furthermore, FIG. 2 illustrates that the sample injector includes a robot arm 280 which is configured for moving the injection needle 202. FIG. 2 shows the sample injector in an operation mode in which the injection needle 202 is connected to the robot arm 280. In this operation mode, it is possible for the robot arm 280 to move the injection needle 202 between the fluid container 214 containing the fluid on the one hand and the seat 200 on the other hand. In FIG. 2, the robot arm 280 presently moves in such a direction so as to insert the needle 202 into the seat 200 for subsequently injecting a fluid which has previously been aspirated by the injection needle 202 into the fluidic path between pump 20 and separation column 30. In this configuration of FIG. 2, the injection needle 202 is mounted temporarily on a needle mounting unit 282 of the robot arm 280.

Figure 3:
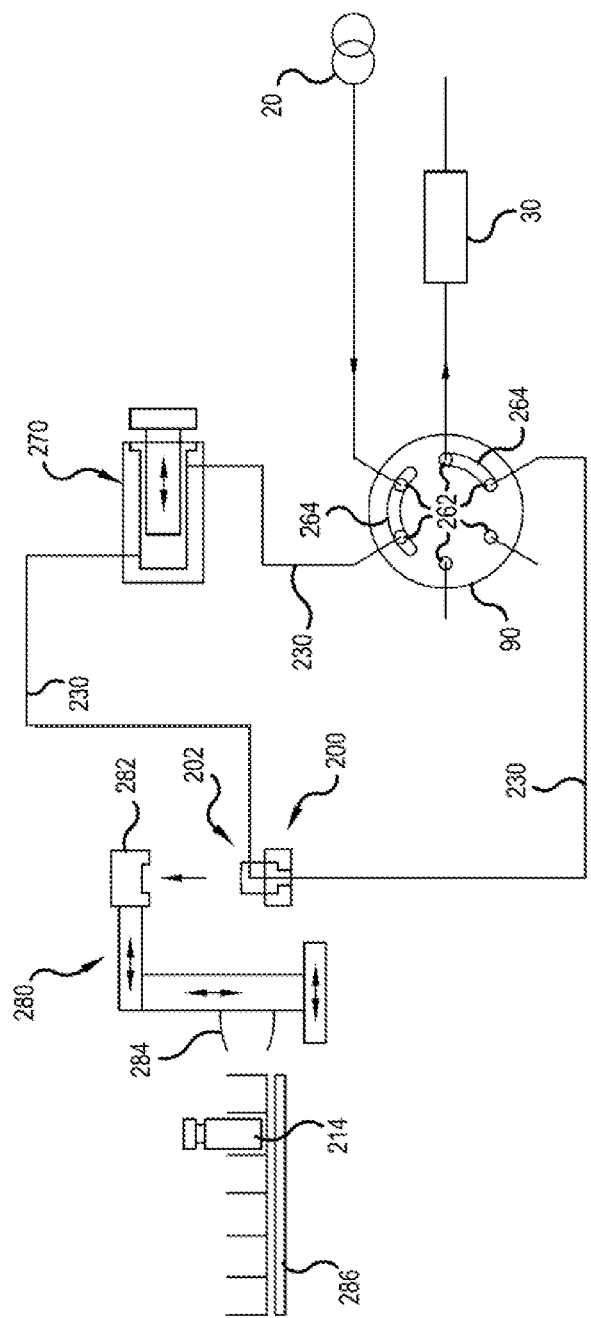

After having completed the downward motion of the robot arm 280 (together with mounted needle 202) and the needle 202 has been inserted into the seat 200, the needle 202 is selectively disconnected from the needle mounting unit 282 and therefore from the robot arm 280 so that the injection needle 202 remains accommodated in the seat 200 and is now separate from the robot arm 280, compare FIG. 3.

In the scenario of FIG. 3, the fluidic switch 90 can be switched so that the fluid which has previously been injected in the needle 202 is transferred into a fluidic path between the pump 20 and the separation column 30. During the time interval in which this injection procedure is carried out, the robot arm 280 is free to be used for any other task.

Figure 4:
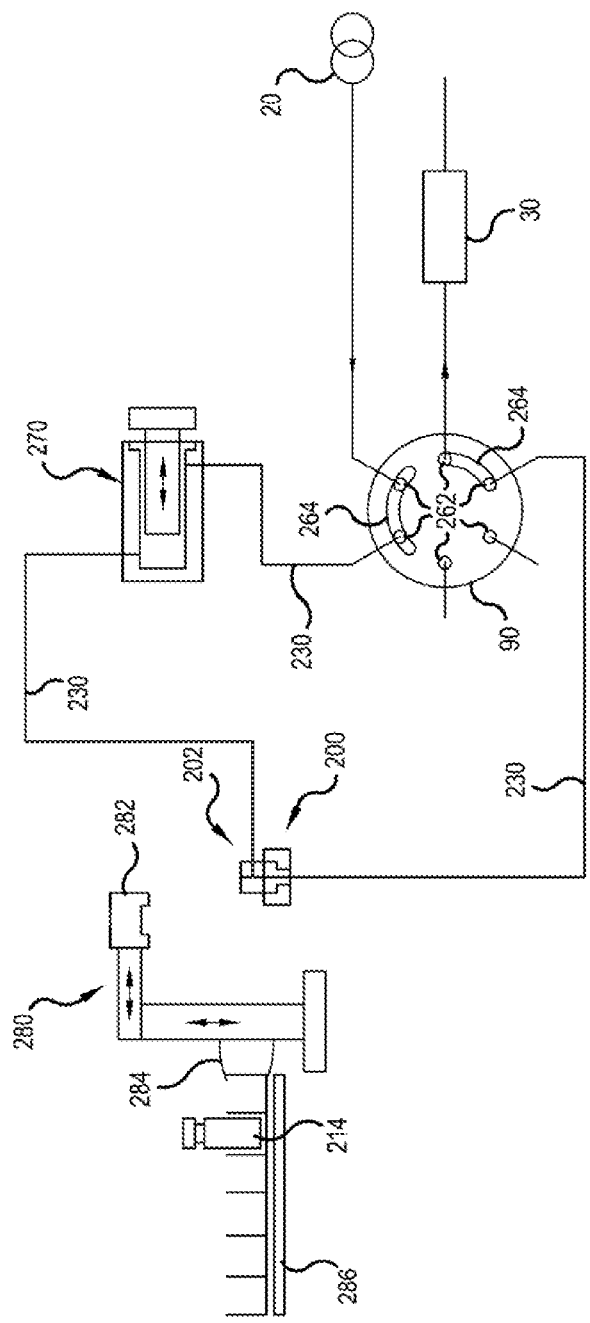

For instance, as shown in FIG. 4, the robot arm 280, now being disconnected from the needle 202, can be moved towards the fluid container 214 so that a fluid container gripping unit 284 (illustrated in FIG. 2 to FIG. 4 as some kind of clamping mechanism) is capable to grip the fluid container 214 for handling it. For instance, the fluid container 214 may be placed on a specific fluid container support 286 so as to be located at a defined position so that the needle 202 can be moved towards the fluid container 214 for aspirating the fluid (the latter operation mode is not shown in the figures).

In the following, referring to FIG. 5 and FIG. 6, a sample injector 500 for injecting a fluid into a fluidic path according to an exemplary embodiment will be explained.

The sample injector 500 comprises a robot arm 502 which is configured for moving an injection needle 506. The latter may be attached to an injection needle holder 504 of the robot arm 502 for a moving operation. Such a moving operation of an injection needle 506 which in the operation mode shown in FIG. 5 and FIG. 6 is presently disconnected from the robot arm 502, can be performed between a fluid container containing a fluid to be aspirated into the injection needle 506 on the one hand and a seat 508 in fluid communication with the fluidic path (into which the fluid is to be subsequently injected) on the other hand.

Figure 5:
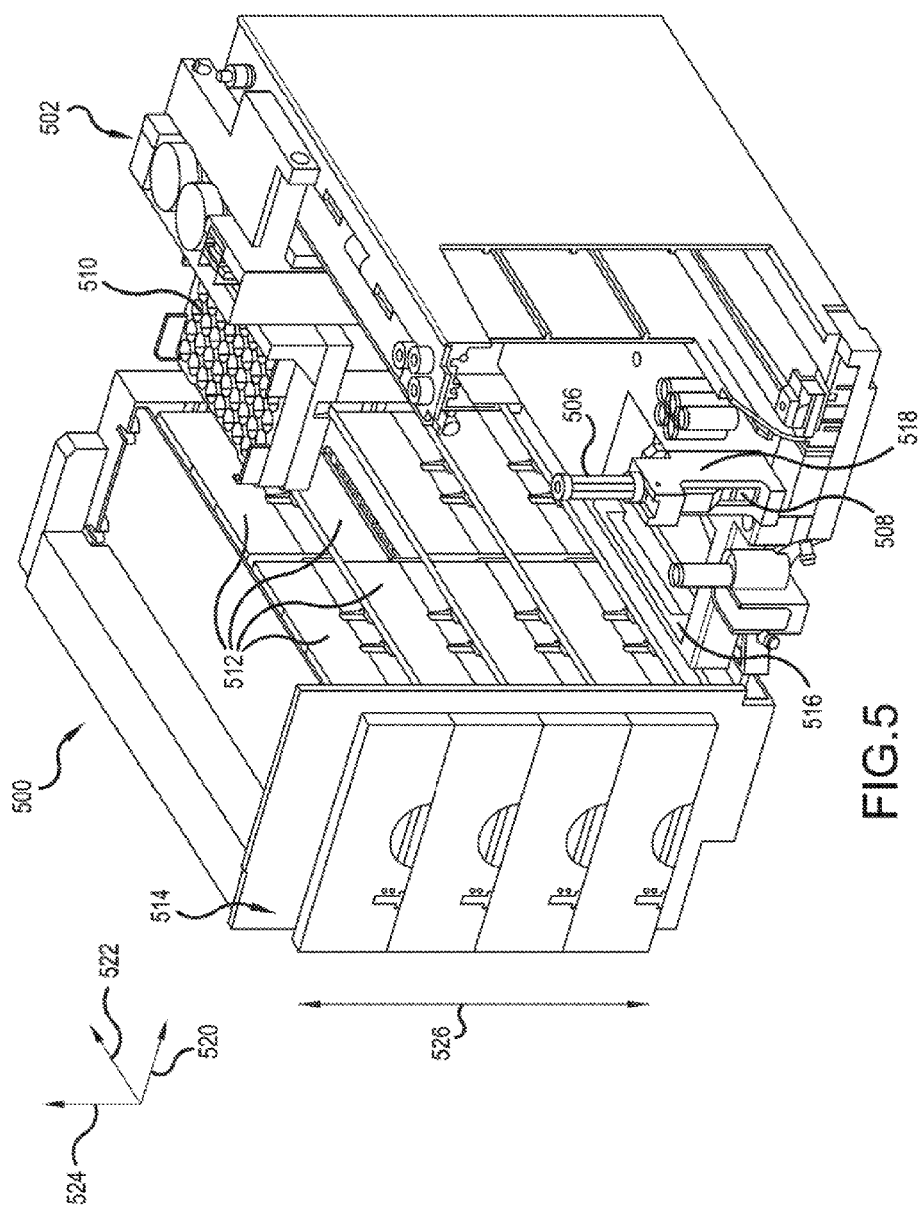
FIG. 5 is a first view of a sample injector system according to an exemplary embodiment of the invention showing a robot arm and a fluid container rack.
Figure 6:
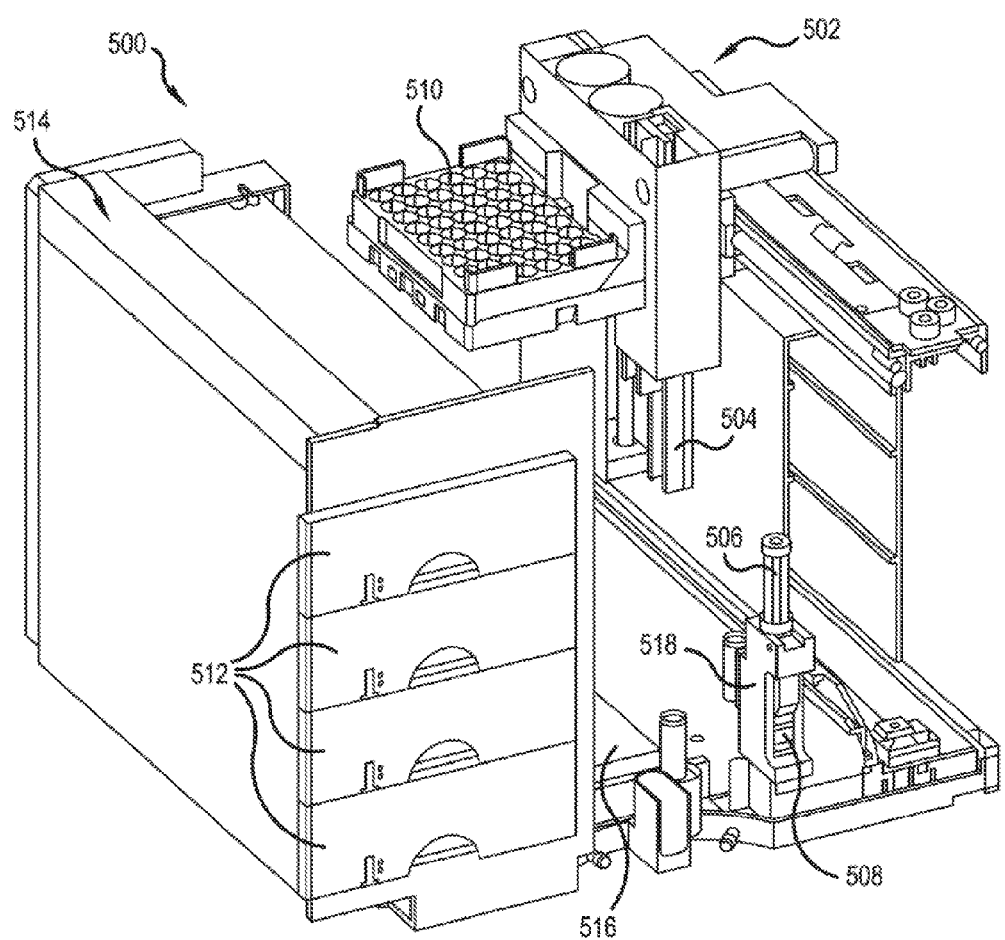
FIG. 6 shows a second view of the sample injector of FIG. 5.

Such a motion of the needle 506 held by the robot arm 502 can be better seen from the illustrations of a robot arm 502 of a sample injector 500 in FIG. 7 to FIG. 10 (the sample injector 500 of FIG. 5 to FIG. 6 is very similar to the one of FIG. 7 to FIG. 10).

Figure 8:
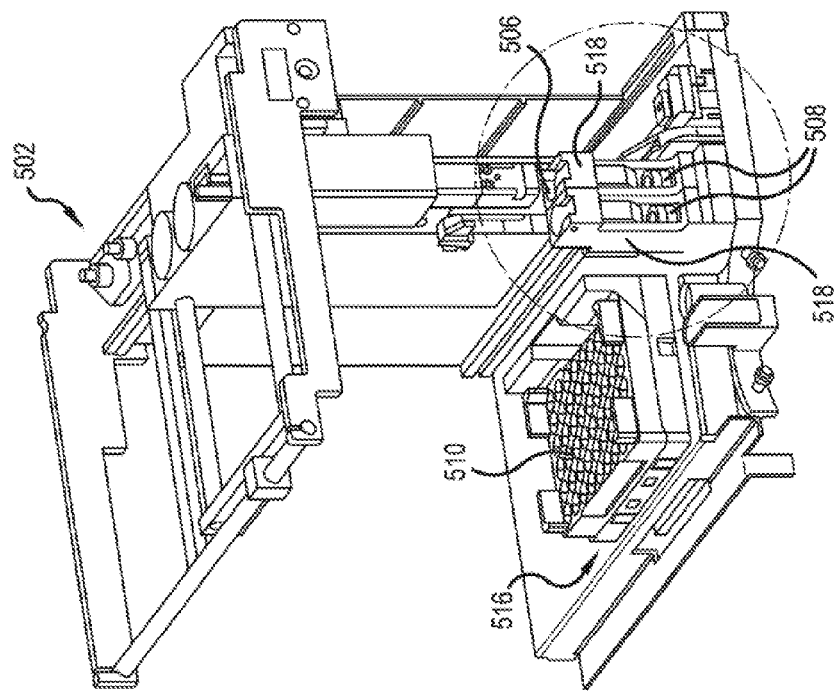
FIG. 7 and FIG. 8 show two different views of a robot arm serving a well plate together with two needle park stations of a sample injector according to an exemplary embodiment of the invention.
Figure 7:
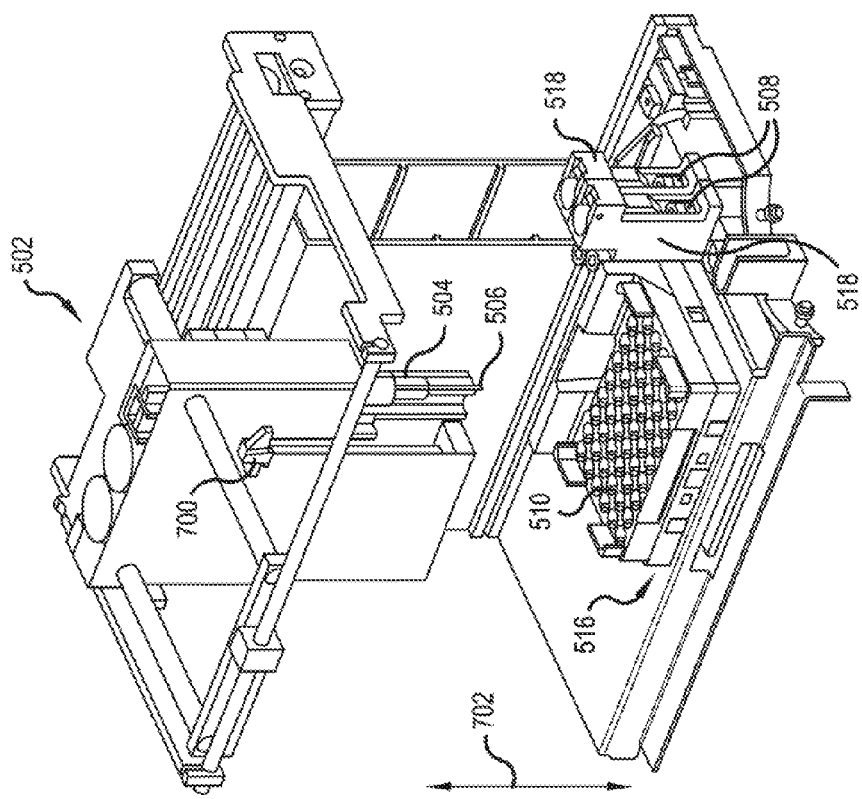
Figure 9:
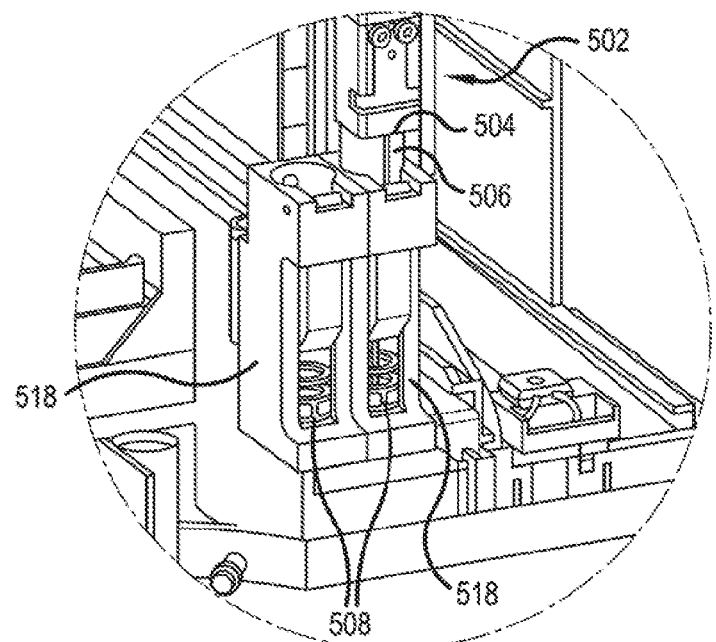
FIG. 9 shows a detail of the sample injector of FIG. 8 illustrating the needle park station in cooperation with the robot arm.
Figure 10:
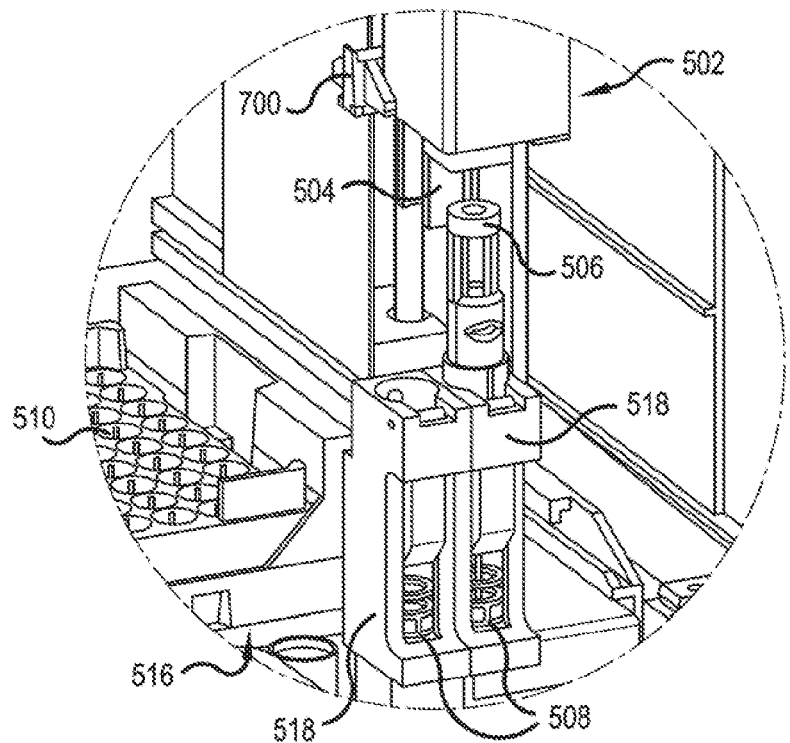
FIG. 10 shows another detailed view of the needle park station of the sample injector of FIG. 8 in an operation mode in which the needle is disconnected from the robot arm.

FIG. 7 shows needle 506 attached to the robot arm 502 so that needle park stations 518 and seats 508 are empty. FIG. 8 shows how the needle 506 is disconnected from the robot arm 502 and inserted in one of the needle park stations 518. FIG. 9 shows a detail of the scenario of FIG. 8. FIG. 10 shows a scenario similar to FIG. 9 in which the needle 506 is disconnected from the robot arm 502.

Figure 13:
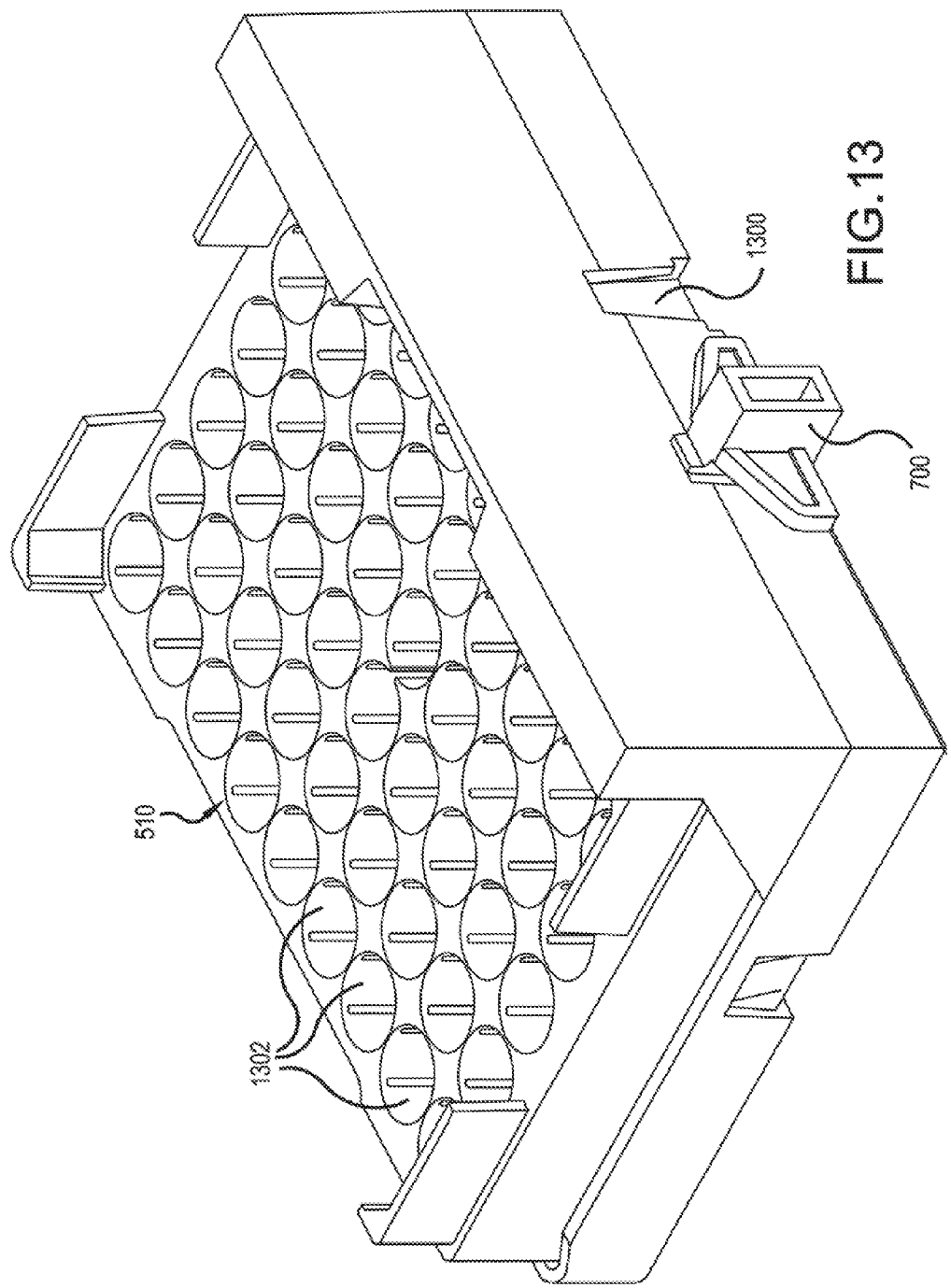
FIG. 13 illustrates a well plate as an example for a fluid container having a coupling for a robot arm according to an exemplary embodiment of the invention.

FIG. 7 shows a well plate 510 having a plurality of fluid containing recesses (also denoted as wells) each configured for receiving a corresponding fluid (such as a biological sample, a solvent, etc.). In the operation modes of FIG. 5 and FIG. 6, the sample plate 510 is handled by the robot arm 502, i.e. a well plate holder of the robot arm 502 is presently connected to the sample plate 510 (or well plate). The well plate holder can be brought in engagement with a correspondingly configured connection piece 1300 of the sample plate 510, which can be best seen in FIG. 13, located at a lateral surface of the sample plate 510.

Thus, the robot arm 502 can be used in a first operation mode in which it takes a sample plate 510 (such as a microtiter plate) out of one of a plurality of sample plates which are presently accommodated in a horizontally and vertically stacked manner in different compartments 512 of a fluid container rack 514 which can be best seen in FIG. 5. The well plate rack 514 is operable with a push loading drawer mechanism. In other words, the robot arm 502 may be moved along three perpendicular directions to access any desired position in a three-dimensional space, i.e. has a mechanism to move along two horizontal directions 520, 522 and one vertical direction 524, so as to able to take a selected one of the well plates 510 out of a corresponding well plate compartment 512 of the fluid container rack 514 and to place it on a correspondingly dimensioned and located well plate support 516, i.e. a specifically defined surface area of the sample injector 500 on which the well plate 510 may be placed by the robot arm 502 for further operation.

When the well plate 510 is placed on the well plate support 516, the robot arm 502 may disconnect from the previously moved well plate 510. After this, the robot arm 502 may then move to a needle 506 which is presently parked in a seat 508 and at a needle park station 518 (compare FIG. 5 or FIG. 10). The robot arm 502 may then take up such a needle 506 by attaching or connecting it to the injection needle holder 504. Subsequently, the robot arm 502 may take along the needle 506 and may move it to the well plate support 516 so that the needle 506 may be immersed into fluid of a corresponding well of the well plate 510 for aspirating such a fluid, i.e. for sucking such a fluid into a capillary of the needle 506. It is also possible that taking up the needle 506 by the robot arm 502 connects the needle 506 fluidicly to a capillary carried along with the robot arm 502. The fluid volume to be aspirated may be defined by a metering device (such as the one shown in FIG. 2 to FIG. 4) being in fluid communication with the connected capillary. After having aspirated the fluid, the needle 506 being still connected to the injection needle holder 504 of the robot arm 502 may be then moved back into the seat 508 so as to be brought in fluid-tight connection with the seat 508. This procedure may be supported by foreseeing the seat 508 with assigned needle park station 518.

Hence, the robot arm 502 may be operable to contribute to the fluid aspiration of the needle 506 and to its subsequent spatial transfer to the seat 508 for fluid injection while the well plates 510 remain spatially fixed. However, the robot arm 502 may also be operable to contribute to the handling of the well plates 510 between the fluid container rack 514 and the well plate support 516. Since these two tasks are required alternatingly (i.e. one task is needed while the other one is not needed, and vice versa), the resources of the robot arm 502 can be used very efficiently basically without inactive time intervals.

In the embodiment of FIG. 5 and FIG. 6, a single seat 508 with a single assigned needle park station 518 is shown, whereas in the embodiment of FIG. 7 to FIG. 10, two seats 508 and two assigned needle park stations 518 are provided. A skilled person will understand that any desired other number of seats 508/needle park stations 518 may be foreseen so that the robot arm 502 can serve also multiple seats 508, multiple injection needles 506 and multiple needle park stations 518, while simultaneously being capable of serving multiple well plates 510 being stored in the well plate compartments 512 of the well plate rack 514.

After having taken a dedicated well plate 510 from a corresponding well plate compartment 512 of the well plate rack 514 by the robot arm 502 using the well plate holder, the robot arm 502 may move the taken well plate 510 to the well plate support 516. Thereafter the robot arm may move to connect to a needle 506 (which may be presently stored in a corresponding seat 508 and fastened by a needle park station 518) via the injection needle holder 504. Then, the robot arm 502 having the connected (but disconnectable) injection needle 506 at the injection needle holder 504 may move to a dedicated well (shown with reference numeral 1302 in FIG. 13) which is filled with a fluid such as a sample or a solvent. The injection needle 506 may then aspire such a fluid from a corresponding well 1302 of the well plate 510. The so aspired fluid may then be injected into a selectable seat 508, or more precisely into a fluid conduit connected thereto for injecting the sample or solvent into a fluidic path between a pump 20 and a separation column 30, as shown in FIG. 1. For this purpose, the robot arm 502 moves the injection needle 506 connected to the injection needle holder 504 towards the corresponding seat 508/needle park station 518. Upon vertically lowering the injection needle 506 connected to the injection needle holder 502 by a downward motion of the robot arm 502, the injection needle 506 will insert into a reception hole of the needle park station 518, will therefore be brought in fluid-tight engagement with the seat 508 and will be automatically disconnected from the injection needle holder 504 and connected to a corresponding supporting element of the needle park station 518.

Hence, the injection needle 506 is configured for aspirating the fluid from the fluid container 510, when the injection needle 506 has been moved to the fluid container 510, and is configured for injecting aspirated fluid into the fluidic path when the injection needle 506 is accommodated in the seat 508. The seat 508 is configured for accommodating the injection needle 506 and for providing fluid communication with the fluidic path. The robot arm 502 in turn is configured for selectively disconnecting the injection needle 506 from the robot arm 502 when the injection needle 506 is accommodated in the seat 508. While the injection needle 506 remains accommodated in the seat 508 held by the needle park station 518, the robot arm 502 is free for performing a further task while the injection needle 506 remains disconnected from the robot arm 502. This further task may for instance be the well plate handling mentioned above in which the robot arm 502 handles a well plate 510, i.e. takes a certain well plate 510 out of a corresponding well plate compartment 512 of the well plate rack 514, and places the well plate 510 on the well plate support 516. It is also possible that the robot arm 502, in this time interval, puts back a well plate 510 which is presently located on the well plate support 516 into the corresponding compartment 512 of the well plate rack 514.

In the embodiment of FIG. 7, FIG. 8, FIG. 9, and FIG. 10, in which multiple seats 508/needle park stations 518 and multiple needles 506 are present, the robot arm 502 may also serve another needle 506, another seat 508 and/or another needle park station 518 while the fluid which has been aspirated into a needle 506 is presently injected via the seat 508 into one of fluidic paths.

When the injection needle 506 is accommodated in the seat 508, there is a fluid-tight connection or a pressure-tight connection between the injection needle 506 and the seat 508 so that the aspirated fluid may be injected into the fluidic path without leakage.

The needle park station 518 retains the injection needle 506 while the injection needle 506 remains accommodated in the seat 508. An advantageous feature of the sample injector 500 is also that the robot arm 502, the injection needle 506, the seat 508 and the needle park station 518 cooperate for sealing the fluid conduit of the injection needle 508 with regard to an environment upon disconnecting the injection needle 506 from the robot arm 502. In other words, when the robot arm 502 moves upwardly after having inserted the still connected injection needle 506 into the seat 508 and to the needle park station 518, a subsequent upward motion of the robot arm 502 will not only detach the injection needle 506 from the injection needle holder 504 of the robot arm 502 which is then free for serving other tasks, but at the same time an upper end of the injection needle 506 will be sealed so that the aspirated fluid may be injected in a downward direction into the seat 508 by a sucking operation. Furthermore, when the needle 506 is parked in the needle park station 518 and is in fluid-tight connection with the seat 508, the robot arm 502 will simply move downwardly again and will operate a locking mechanism so as to unlock the needle 506 from the needle park station 518 and the seat 508, and will simultaneously connect to the injection needle 506 by the injection needle holder 504.

As can be further taken from FIG. 5, the robot arm 502 may be moved along first horizontal direction 520, second horizontal direction 522 (perpendicular to first horizontal direction 520) and third vertical direction 524. In the vertical direction 524, the robot arm 502 has two separately and independently operable lift mechanisms. A first lift mechanism is configured for handling the well plates 510, i.e. for taking out a dedicated well plate 510 from a corresponding well plate compartment 512 of the well plate rack 514 to the well plate support 516 and/or for putting it back from the well plate support 516 to a corresponding well plate compartment 512 of the well plate rack 514. Therefore, the first lift mechanism of the robot arm needs to be capable of operating over a first stroke length which is indicated schematically in FIG. 5 with reference numeral 526 and which may basically correspond to the height of the well plate rack 514. On the other hand, the robot arm 502 has a second lift mechanism configured for handling the injection needle 506 over a second stroke length along the vertical lift axis 524. Thus, for operating the needle 506 between a first operation mode in which it is immersed in a well 1302 of the well plate 510 and a second operation mode in which it is placed in the seat 508, the needle 506 may also be lifted for being moved along the arrangement, as can best be seen in FIG. 7. A corresponding second stroke length is indicated schematically with reference numeral 702. As can be taken from a comparison of FIG. 5 and FIG. 7, the first stroke length 526 is larger than the second stroke length 702. The robot arm 502 is hence configured so as to be capable of operating the well plate holder along the first stroke length 526 and the injection needle holder 504 along the second stroke length 702.

Figure 11:
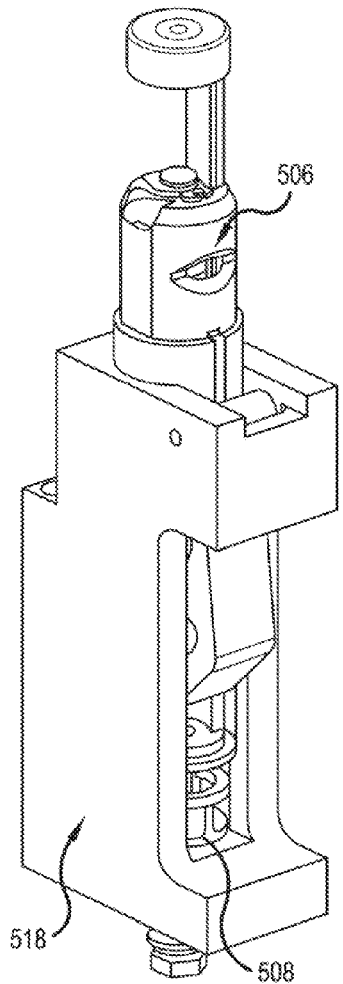
FIG. 11 and FIG. 12 are two different images illustrating a needle park station of a sample injector with a connected needle according to an exemplary embodiment of the invention in a three dimensional view and in a cross-sectional view.

FIG. 11 shows a three-dimensional view of a needle park station 518 together with a corresponding seat 508 and a cartridge-type injection needle 506 which has presently been disconnected from the robot arm 502, more precisely from the injection needle holder 504 of the robot arm 502.

Figure 12:
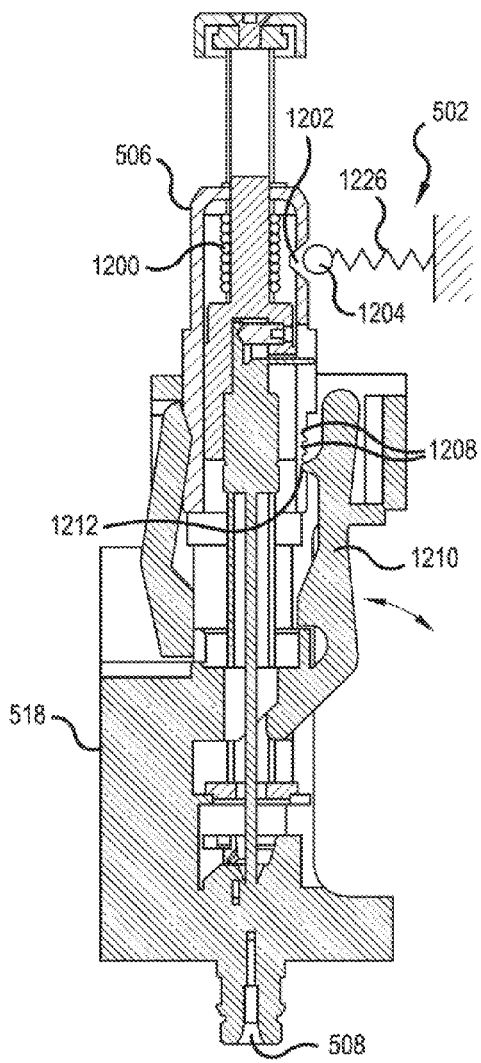

FIG. 12 shows a cross-sectional view corresponding to FIG. 11 and will be described in more detail in the following in terms of the combined locking-unlocking mechanism involved in the transfer of the needle 506. The robot arm 502 (only a part thereof is shown schematically in FIG. 12), the seat 508 and the needle park station 518 now cooperate so that upon inserting the injection needle 506 into the seat 508 by the robot arm 502, a biasing spring 1200 of the injection needle 506 is biased to as to exert a sealing force between the injection needle 506 and the seat 508. Additionally, a mutual locking mechanism of the injection needle 506 and the needle park station 518 is activated. For this purpose, the robot arm 502 and the injection needle 506 comprise cooperating first retaining elements configured for retaining the injection needle 506 at the robot arm 502 with a first retaining force while the injection needle 506 is outside the seat 508. These first retaining elements can be realized by a latching recess 1202 of the injection needle 506 and a corresponding latching ball (or other protrusion) 1204 configured for engaging the latching recess 1202. A further biasing spring 1226 of the robot arm 502 may press the latching ball 1204 into the latching recess 1202 for exerting the first retaining force.

Furthermore, the needle park station 518 and the injection needle 506 comprise cooperating second retaining elements configured for retaining the injection needle 506 at the needle park station 518 with the second retaining force being larger than the first retaining force and being operable when the injection needle 506 is inserted into the seat 508 so that subsequently retracting the robot arm 502 from the seat 508 releases the injection needle 506 from the robot arm 502 and retains the injection needle 506 at the needle park station 518. These second retaining elements can be realized by further latching recesses 1208 of the injection needle 506 and a pivotable retaining lever 1210 which can be pivoted in a way as indicated by an arrow in FIG. 12 and which has a protrusion 1212 for engaging one of the one or more latching recesses 1208. Thus, the mutual locking mechanism is provided by the second retaining elements 1208, 1210, 1212. Apart from this, a latch may be provided which may be actuated by the robot arm 502 to disengage the second retaining elements 1208, 1210, 1212 from one another so that subsequently retracting the robot arm 502 pulls the injection needle 506 along with the robot arm 508.

Therefore, the described mechanism results in the fact that when the injection needle 506 is still connected to an injection needle holder 504 of the robot arm 502 and will be placed in the seat 508, it will be disconnected from the injection needle holder 504 upon retracting the robot arm 502 upwardly. At the same time, the injection needle 506 will be locked to the needle park station 518 so as to provide for a secure connection between seat 508 and needle 506. Furthermore, an upper end portion of the needle 506 is sealed so that aspirated fluid in the capillary of the needle 506 can subsequently be injected into the fluidic path connected to the seat 508.

Figure 14:
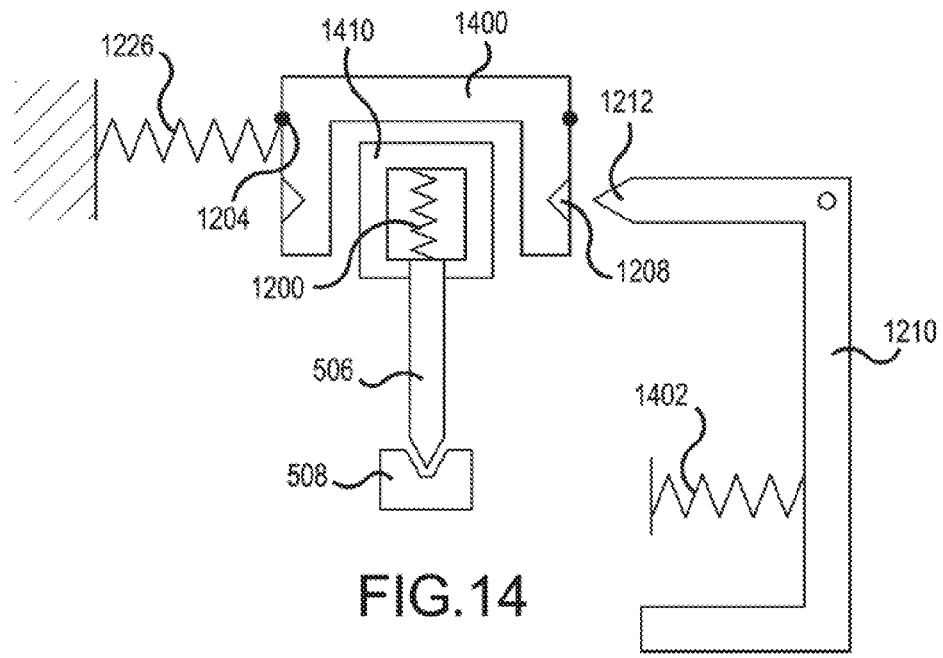
FIG. 14 is a schematic view showing a mechanism of operating a needle cartridge by a robot arm together with a needle park station.

FIG. 14 is a schematic illustration of the combined locking and unlocking mechanism described referring to FIG. 12 and specifically shows that the injection needle 506 is arranged within a package denoted schematically with reference numerals 1400, 1410. Furthermore, FIG. 14 shows that an additional spring 1402 can be provided for biasing the lever 1210 so that the protrusion 1212 will be forced into the recess 1208.

Figure 15:
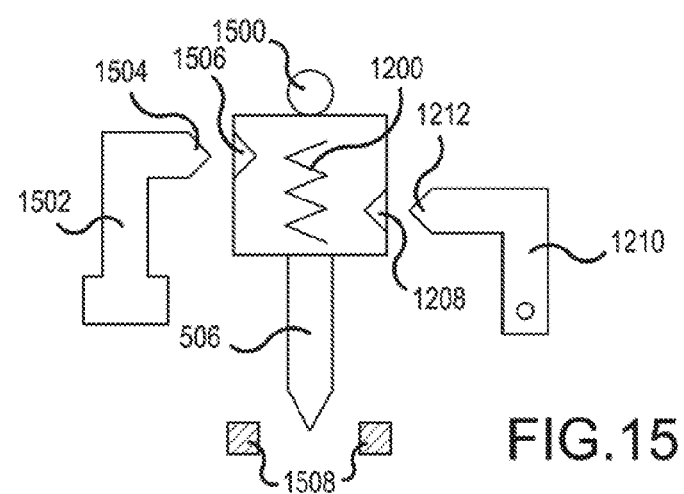
FIG. 15 schematically illustrates an example as to how a disconnection of an injection needle can be performed.

FIG. 15 shows a part of the schematic arrangement of FIG. 14 and additionally shows a shaft or actuator 1500 of the injection needle 506. Furthermore, as compared to the ball 1204 and the spring 1226, the connection between robot arm 502 and the injection needle 506 may in this embodiment be realized by a lever 1502 having a protrusion 1504 cooperating with a recess 1506 in the package of the needle 506.

As can furthermore be taken from FIG. 15 schematically, the robot arm 502 may comprise a stripper tool 1508 configured for stripping off a fluid container (not shown in FIG. 15) from the injection needle 506 after having aspirated the fluid from the fluid container. Such a stripper tool 1508 may be advantageous when the needle 506 penetrates a septum or a membrane of a vial (for a sterile storage of the fluid), so that after having aspirated fluid from the vial, it may happen that the injection needle 506 may remain connected to the vial. The stripper tool 1508 will then allow the needle 506 to be retracted from the vial.

Figure 16:
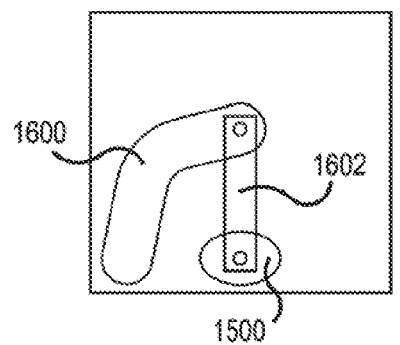
FIG. 16 schematically illustrates a force reduction principle for reducing a handling force exerted by a robot arm for operating a disconnectable needle.

FIG. 16 schematically shows how the shaft 1500 (such as a camshaft) can cooperate with a curved recess 1600 via a force transmission lever 1602. By taking this measure, the injection needle 506 having the lever mechanism shown in FIG. 16 is operable by the robot arm 502 with a reduced force exerted by the robot arm 502 required for sealing the fluid conduit by lever action.

More generally, a force required to be exerted by the robot or robot arm for sealing the needle may be reduced by implementing a force transmission which may use a guide rail, thereby benefiting from a lever action effect.

In the following, referring to FIG. 17 to FIG. 22, a sample injector 500 being very similar to the above-described sample injectors 500 according to an exemplary embodiment of the invention will be explained.

Generally, the sample injector 500 provides for a combined plate handler and sample injection robot. The autosampler 500 shown in FIG. 17 has the advantage to increase sample capacity to more than 400 vials or eight or more well plates. Furthermore, it is possible to handle vials but also well plates with the sample injector 500. Additionally, the sample injector 500 has a very low internal volume to allow fast analysis.

In a concept, where the sample needs to be transported to the sampling unit, it would be difficult to handle well plates. In another concept, where the needle moves to the sample, a long connection capillary is required due to the increased amount of sample plates which has to be addressed. The plate handler or sample injector 500 of FIG. 17 combines the advantages of both systems. It contains a coupling device for pallets. With this coupling mechanism, pallets containing the sample trays can be transported from/to a hotel system (fluid container rack 514) to a parking station (fluid container support 516) inside the autosampler 500. The hotel system contains a plurality of pallets with random access. The plate handler also contains a holding mechanism for the injection needle 506. When a pallet with the sample tray is placed on the parking station, the robot (which is also denoted as robot arm 502) moves a needle 506 to the according sample for sample aspiration.

An advantage of such a combined plate/needle movement system is that only one x, y, z robot system is needed for the plate and for the needle movement. The injection needle only has to be moved in the area of one plate (plate on park station). Thus, a short connection capillary between a needle and sampling unit can be achieved. With the x, y movement of only one well plate, the robot is available to reach two stacks of pallets with its coupling mechanism. Thus, in the described embodiment, a sample capacity of 2 stacks each having 6 sample trays can be accessed. Since the sampling needle is movable, the needle can be cleaned in a needle wash port, if desired or required.

Figure 17:
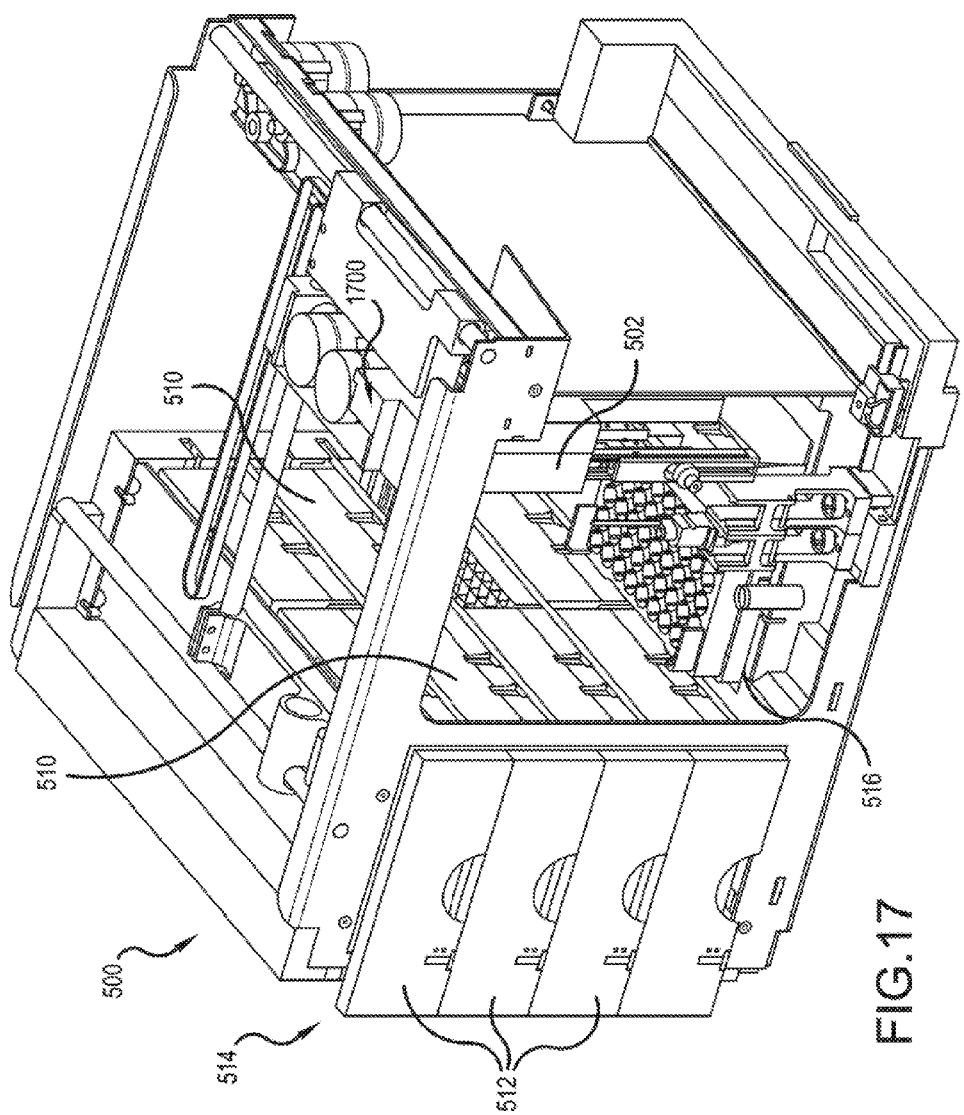
FIG. 17 shows a three-dimensional view of a sample injector according to an exemplary embodiment of the invention.

The x, y, z robot is denoted with reference numeral 1700 in FIG. 17.

Figure 19:
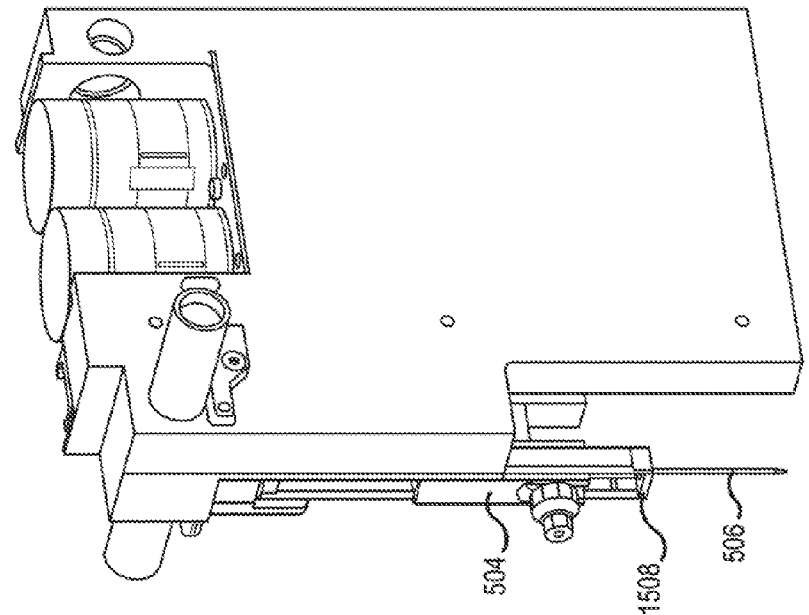
FIG. 19 illustrates a second detailed view of the robot arm of FIG. 18.
Figure 18:
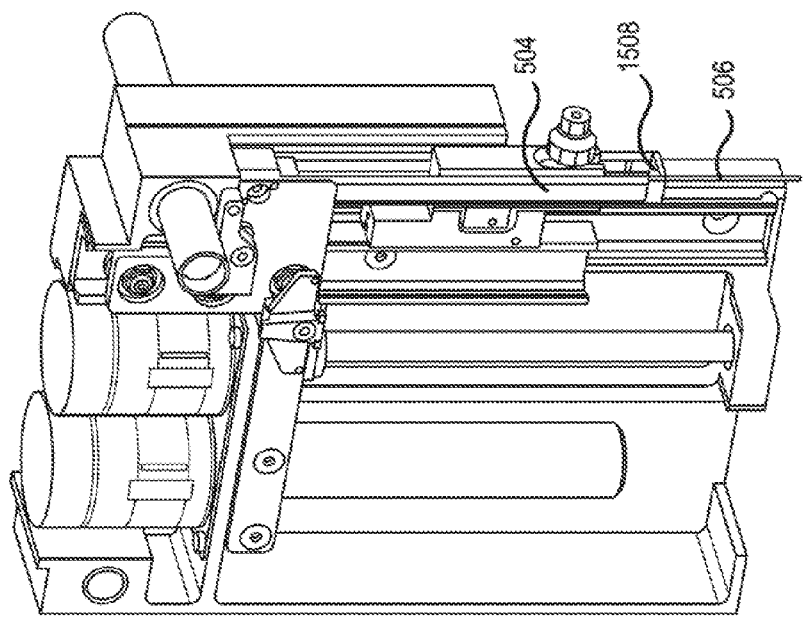
FIG. 18 illustrates a first detailed view of a robot arm of the sample injector of FIG. 17.

FIG. 18 and FIG. 19 show detailed views of the robot arm 1700 wherein the injection needle is denoted with reference numeral 506 and the stripper arrangement with reference numeral 1508.

Figure 20:
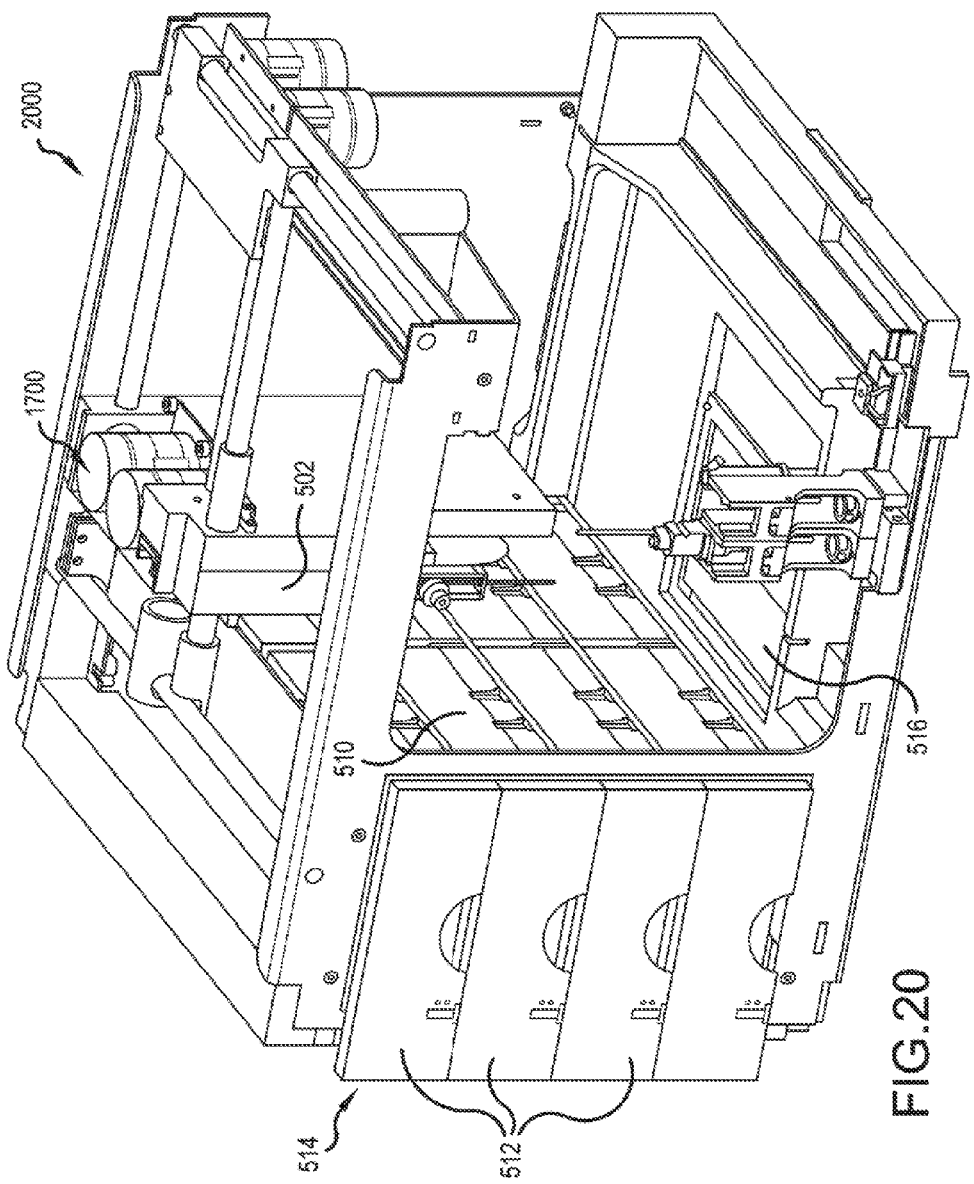
FIG. 20 to FIG. 22 illustrate the sample injector of FIG. 17 in three different operation modes.
Figure 21:
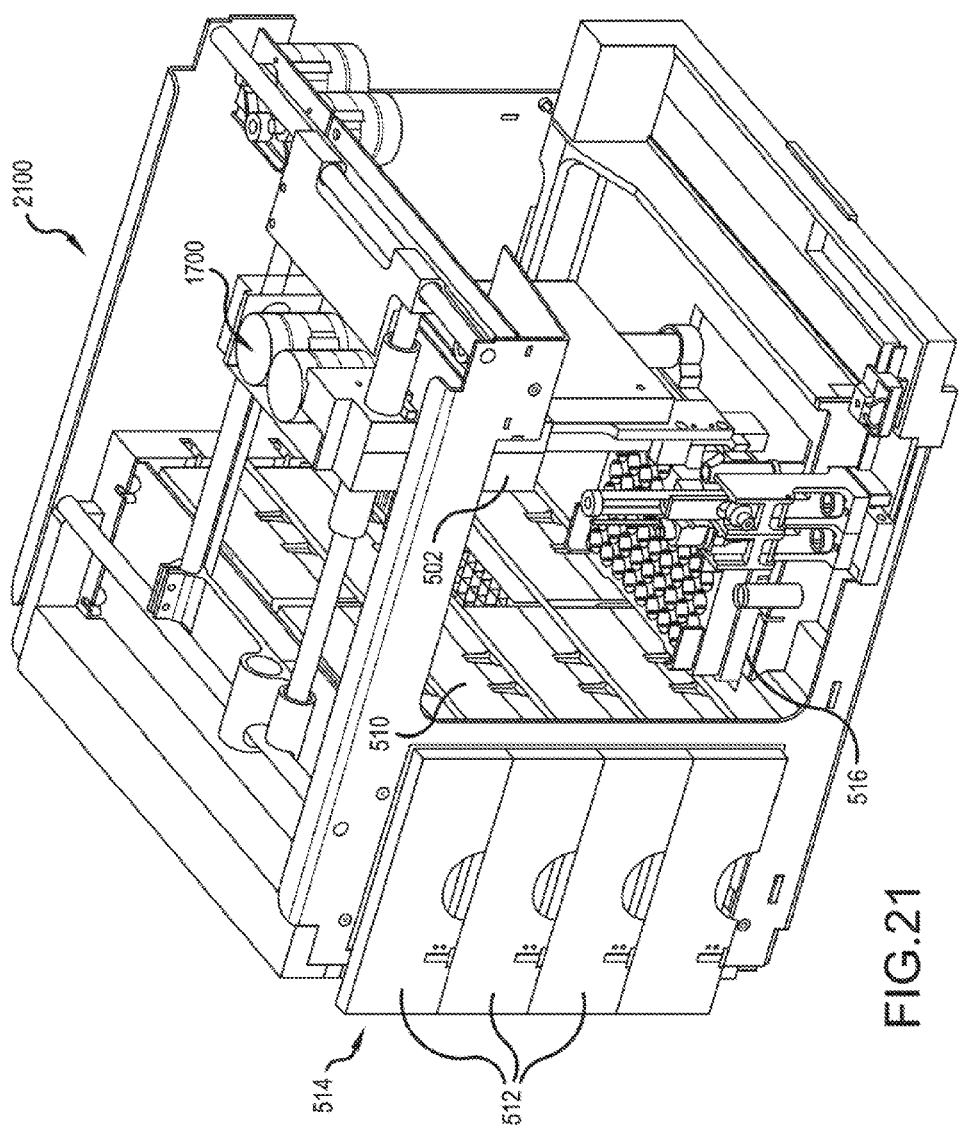
Figure 22:
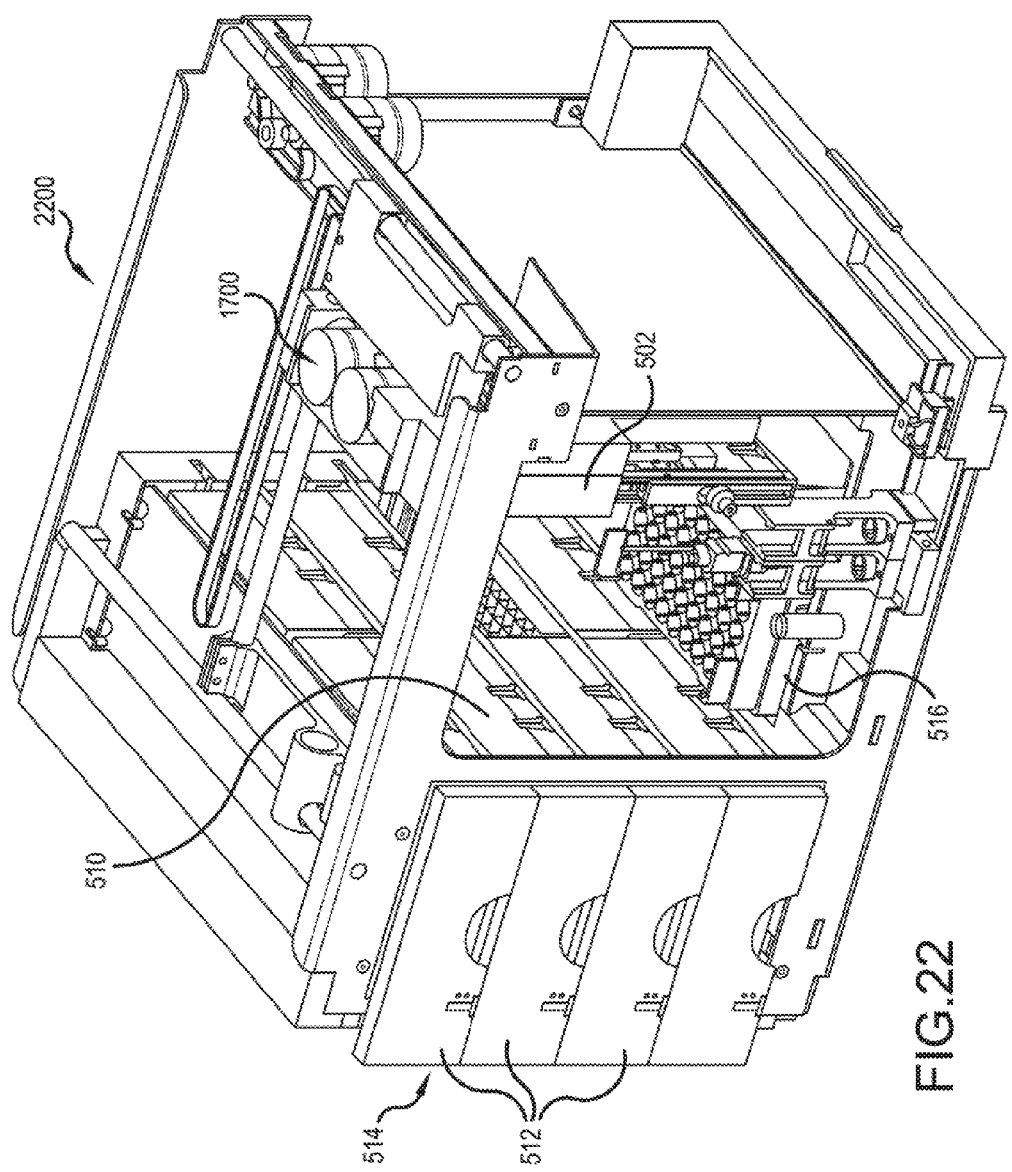

FIG. 20 shows the sample injector of FIG. 17 in a first operation mode 2000 in which the robot moves a palette out of a hotel. FIG. 21 shows the sample injector of FIG. 17 in a second operation mode 2100 in which the robot places the palette on the park station. FIG. 22 shows the sample injector of FIG. 17 in a third operation mode 2200 in which the robot moves the needle to the according sample position to aspirate the sample.

Figure 23:
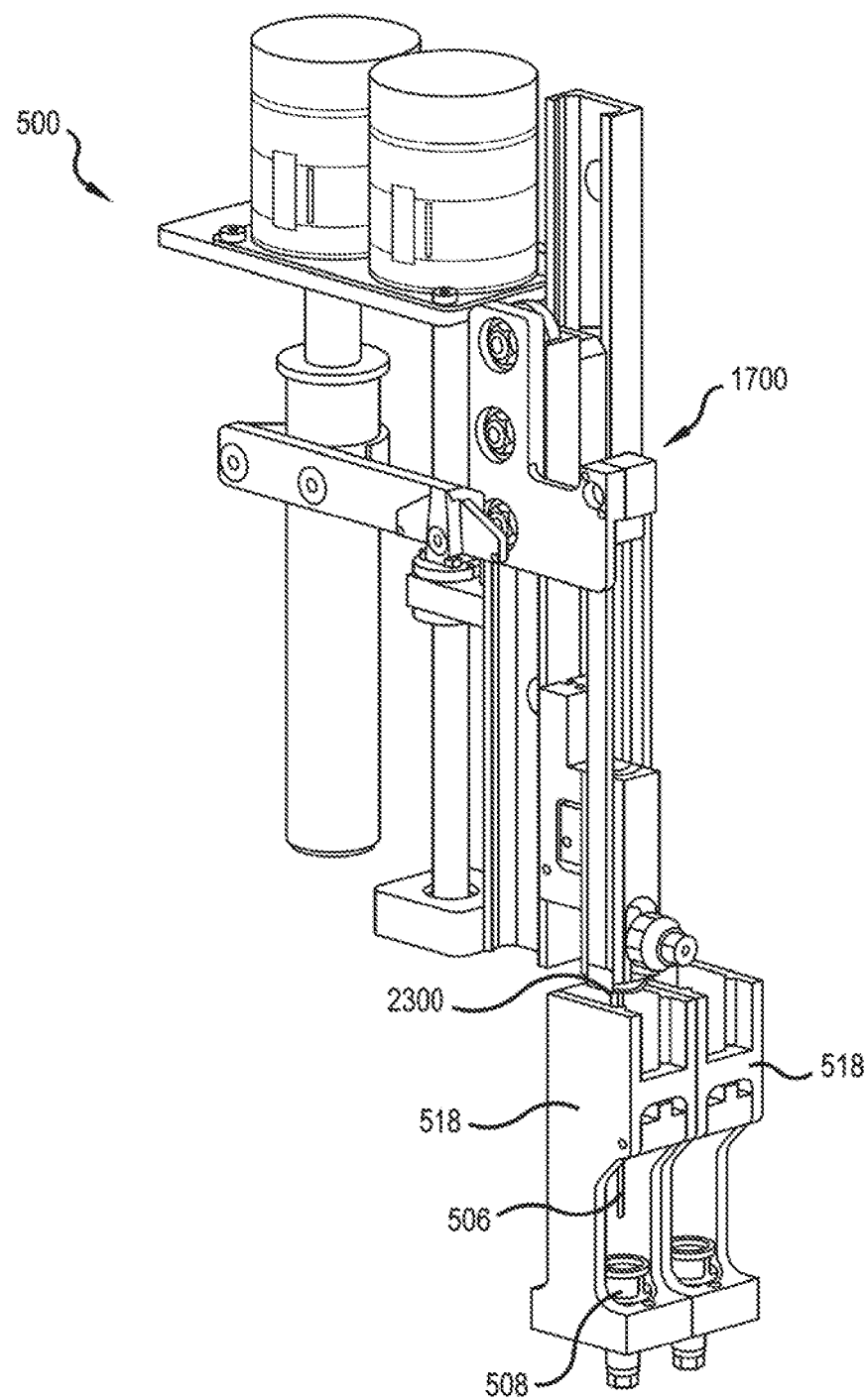
FIG. 23 illustrates a sample injector according to an exemplary embodiment in a three-dimensional view showing details of the sample handling robot arm.

In the following, referring to FIG. 23 to FIG. 25 a sample injector 500 according to still another slightly modified exemplary embodiment will be explained which can be used as a HPLC sample injector with an automatically disconnectable injection needle 506.

A corresponding sample handling robot is able to automatically disconnect the injection needle 506 in a needle park station 518. In this embodiment, the injection needle 506 is coupled to an x, y, z arm via a needle coupler 2300. The needle 506 can be disconnected from the robot arm by a user for exchange purpose or automatically in the needle park station 518. When the needle 506 is disconnected in the needle park station 518, the robot arm is pressing the needle 506 into the needle seat 508 and loads a spring. Then, a locking mechanism may be activated which locks the needle 506 to the needle park station 518 and at the same time opens the lock to the robot arm. Thus, the needle 506 now is sealed in the needle seat 508 by the needle park station 518 and the robot is decoupled from the needle 506. The robot now is able to do other tasks during analysis.

Next, a force amplifying by the needle locking mechanism will be explained. To seal the needle 506 in the needle seat 508, typically a sealing force in the range of 50 to 100 N is needed. Typically, the needle 506 is pressed into the seat 508 via the z-axis of the robot. Thus, a minimal force of 50 to 100 N for the z-drive is needed if the needle 506 is directly coupled to the z-axis of the robot. In an embodiment of a needle coupler, a sealing force amplifying is performed during the decoupling of the needle 506 from the robot. Therefore, the force for the z-drive can be reduced to for instance 30 to 50 N which is a typical force needed for the z-axis to penetrate the septa of the sample vials.

Figure 24:
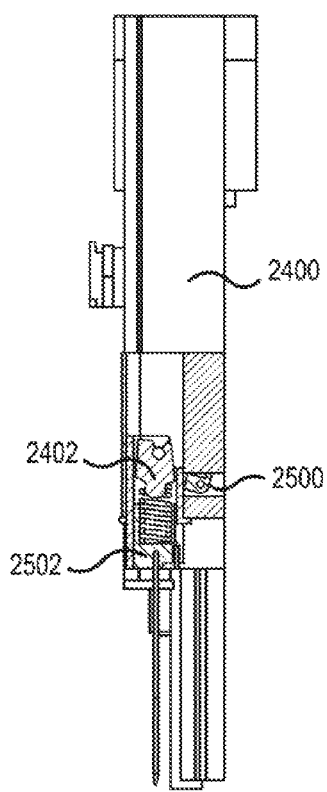
FIG. 24 shows a detailed view of the robot arm of FIG. 24.
Figure 25:
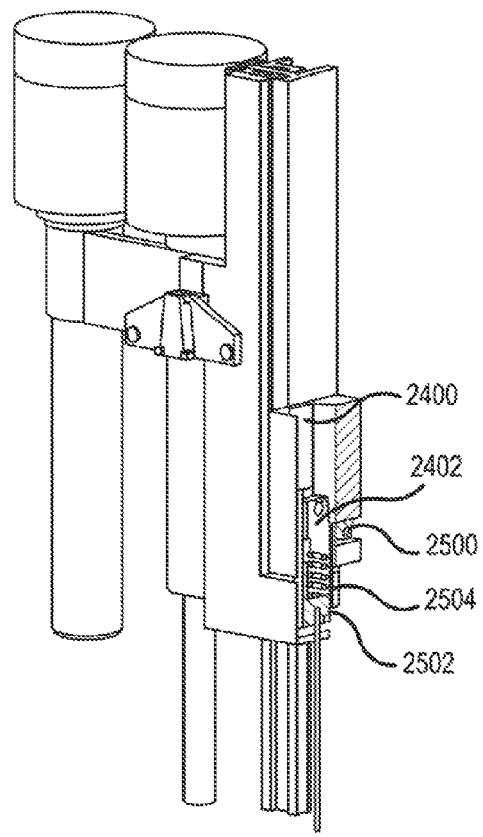
FIG. 25 shows another detailed view of the robot arm of FIG. 24.
Figure 26:
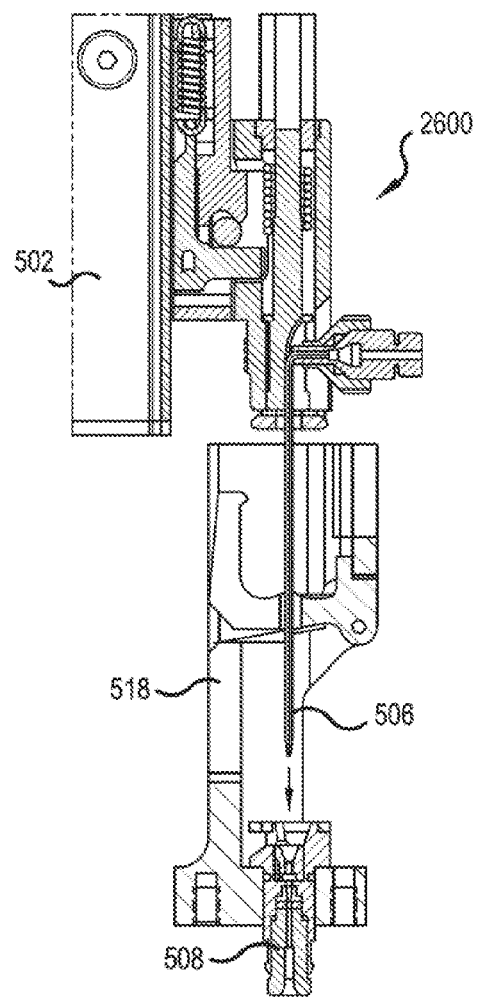
FIG. 26 to FIG. 30 illustrate different operation modes of a needle handling system in which a needle is decoupled from a robot arm and coupled to a needle park station and a seat.

FIG. 24 and FIG. 25 schematically illustrate the function of such a force amplification. The arrangement of FIG. 24 has a robot z-arm 2400, a camshaft 2402 and a camplate. Furthermore, a clamp 2500, a needle holder 2502 and a spring 2504 are shown in FIG. 25.

Inside the needle park station 518, a clamp opens the robot end and at the same time another clamp locks the needle holder 2502 to the needle park station 518. Now, the robot z-arm 2400 is able to move up without a needle 506. During the up movement, the camplate 2404 is activating the camshaft 2402 inside of the needle holder 2502. The camshaft 2402 rotates during the up movement of the robot and loads spring 2504 inside the needle holder 2502 which is pressing the needle 506 down in the needle seat 508.

With this mechanism, a force amplification can be performed. For instance, if the sealing force of 100 N is needed to seal the needle 506 into the needle seat 508, with a camshaft 2402 only ⅕ of the force is needed to load the spring 2504. Of course, a force amplifying during coupling/decoupling the needle 506 to the robot can also be done by another lever mechanism. The camshaft mechanism is only one example.

Advantages of such embodiments of the invention will be explained in the following. A typical analysis time can be in an order of magnitude of 1 min to 60 min. During this time, the needle has to be sealed if the needle seat is flush-through design. Since the robot arm can be decoupled from the needle, the robot is able to do other tasks during this time without disturbing the analysis.

For example, such other tasks which may be done during analysis include the preparation of a next sample plate. If sample plates are stored in a plate hotel, the robot now can place the current sample plate back in the hotel and can prepare the next sample for sample injection. When the next analysis starts, the correct plate already is in place and prepared, which saves time. Another example for such a task is that a next sample can be injected with a second needle. With a second needle and needle park station, the robot already can prepare the next plate, aspirate the sample and place the second needle back in the needle park station. After the analysis is finished in the first needle/needle seat, a valve switches the second needle/needle seat to the analysis path. During analysis with the second needle, the robot handles and injects with the first needle. Therefore, no additional robotic time is added to the sample analysis time. Furthermore, a force amplifying is possible. With for instance a camshaft mechanism, the z-axis of the robot is able to achieve very high sealing loads on the injection needle. Additionally or alternatively, sample preparation and modification can also be performed as an additional task. Since the robot is decoupled from the needle, it can be used for any sample separation and modification, for instance mixing or shaking samples, operating with additional well plate positions like a heater station, barcode reader station or pipetting station. Furthermore, a vial gripper can be foreseen. It is also possible to identify needles or samples with a barcode or a transponder system (such as an RFID system).

Figure 27:
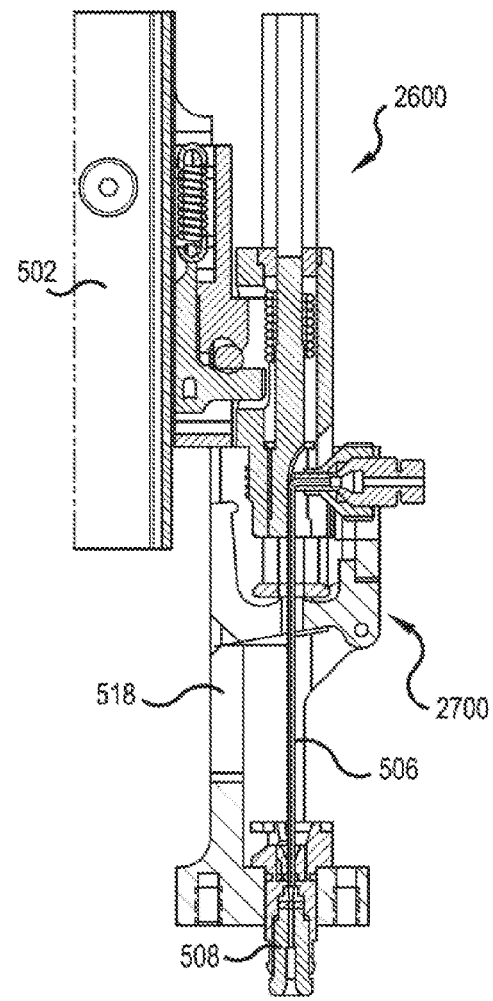
Figure 28:
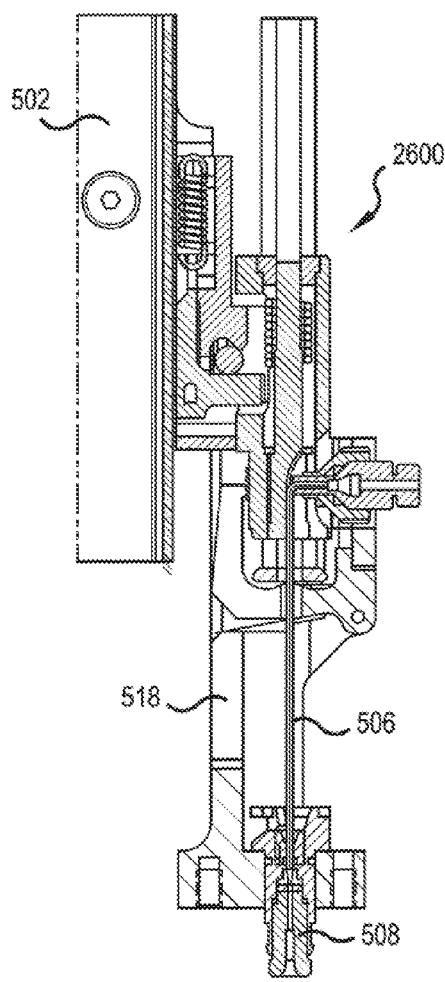
Figure 29:
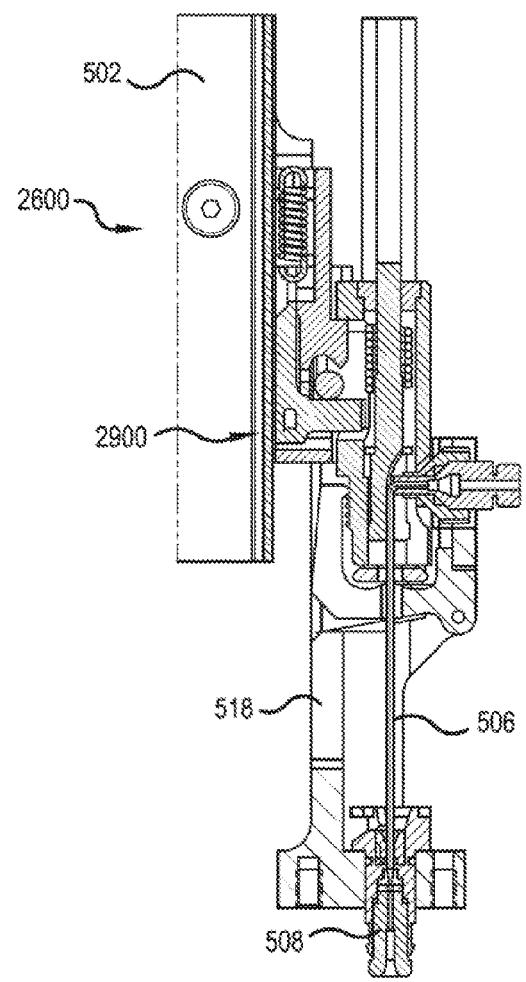
Figure 30:
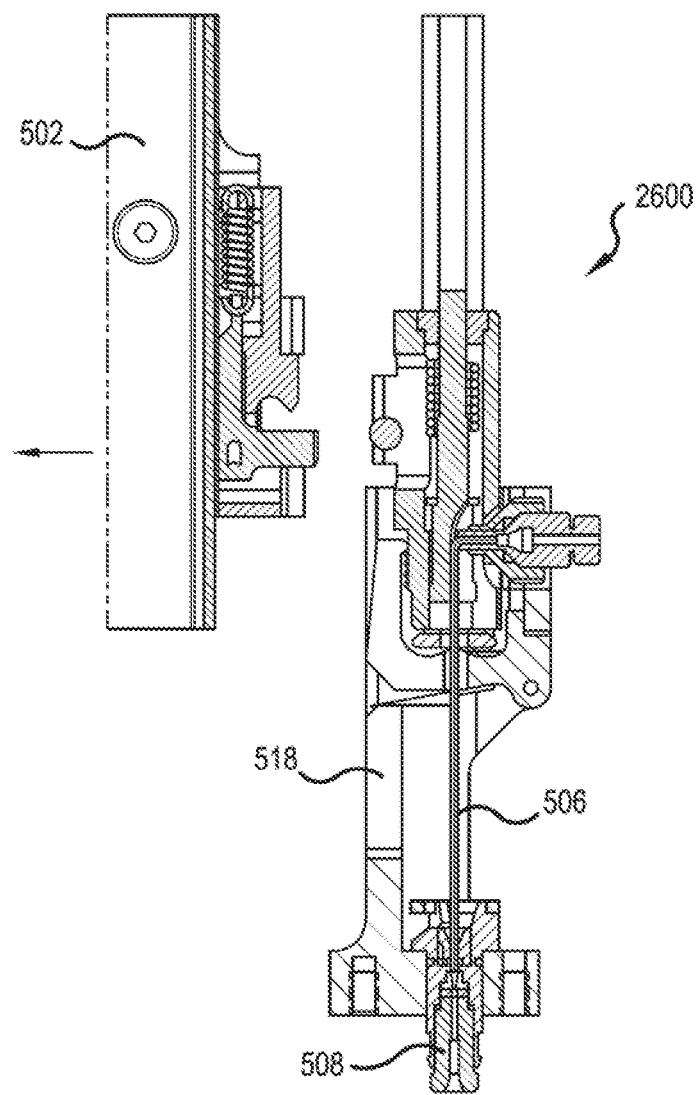

FIG. 26 to FIG. 30 illustrate different operation modes of a needle handling system 2600 in which a needle 506 is decoupled from a robot arm 502 and coupled to a needle park station 518 and a seat 508. The decoupling is performed by a lateral needle decoupling motion In FIG. 26, the robot arm 502 holding the needle 506 approaches the needle park station 518. In FIG. 27, the robot arm 502 has placed the needle 506 in the seat 508 and has accommodated the needle 506 in the needle park station 518. A locking mechanism is opened (see reference numeral 2700). In FIG. 28, the locking mechanism is again closed. In FIG. 29, a coupling mechanism is opened (see reference numeral 2900). In FIG. 30, the robot arm 502 is laterally removed from the needle 506 parked in the needle park station 518.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A sample injector for injecting a fluid into a fluidic path between a high pressure pump and a separation column, the sample injector comprising:
   a robot arm configured for moving an injection needle, when being connected to the robot arm, between a fluid container containing the fluid and a seat in fluid communication with the fluidic path;
   the injection needle configured for aspirating the fluid from the fluid container, when the injection needle has been moved to the fluid container, and for injecting aspirated fluid into the fluidic path, when the injection needle is accommodated in the seat, the injection needle forming a part of the fluidic path when accommodated in the seat;
   the seat configured for accommodating the injection needle and providing fluid communication with the fluidic path;
   wherein the robot arm is configured for selectively disconnecting the injection needle from the robot arm when the injection needle is accommodated in the seat, such that the injection needle remains a part of the fluidic path after being disconnected from the robot arm; and
   wherein the robot arm is configured for performing a further task while the injection needle is disconnected from the robot arm.

2. The sample injector claim 1, wherein the robot arm is configured for performing a fluid handling task while the injection needle is disconnected from the robot arm.

3. The sample injector of claim 1, wherein the robot arm is configured for handling at least one selected of a plurality of fluid containers, each containing a fluid, from a fluid container rack while the injection needle is disconnected from the robot arm.

4. The sample injector of claim 1, wherein the robot arm is configured for being moved or for moving another body while the injection needle is disconnected from the robot arm.

5. The sample injector of claim 1, wherein the robot arm is configured for, while the injection needle is disconnected from the robot arm, serving another injection needle.

6. The sample injector of claim 1, wherein the robot arm is configured for performing the further task under control of a software program.

7. The sample injector of claim 1, wherein the injection needle and the seat are configured to cooperate so that the injection needle is accommodated in the seat in a fluid-tight manner.

8. The sample injector of claim 1, comprising a needle park station configured for retaining the injection needle when the injection needle is accommodated in the seat.

9. The sample injector claim 8, wherein at least a part of the robot arm, the injection needle, the seat and the needle park station is configured to cooperate for sealing a fluid conduit of the injection needle with regard to an environment upon disconnecting the injection needle from the robot arm.

10. The sample injector claim 9, wherein at least a part of the robot arm, the injection needle, the seat and the needle park station is configured so that, upon inserting the injection needle into the seat by the robot arm, a biasing element is biased so as to exert a sealing force between the injection needle and the seat, and a mutual locking mechanism of the injection needle and the needle park station is activated.

11. The sample injector of claim 10, wherein the mutual locking mechanism is provided by the second retaining elements.

12. The sample injector of claim 9, wherein the injection needle comprises a lever mechanism operable by the robot arm for reducing a force to be provided by the robot arm required for sealing the fluid conduit by lever action.

13. The sample injector of claim 8,
wherein the robot arm and the injection needle comprise cooperating first retaining elements configured for retaining the injection needle at the robot arm with a first retaining force being operative while the injection needle is outside the seat; and
wherein the needle park station and the injection needle comprise cooperating second retaining elements configured for retaining the injection needle at the needle park station with a second retaining force being larger than the first retaining force and being operative when the injection needle is inserted into the seat so that subsequently retracting the robot arm from the seat releases the injection needle from the robot arm and retains the injection needle at the needle park station.

14. The sample injector of claim 13, wherein the needle park station comprises a latch being actuatable by the robot arm to disengage the second retaining elements from one another so that subsequently retracting the robot arm pulls the injection needle along with the robot arm.

15. The sample injector of claim 8,
wherein the robot arm and the injection needle comprise cooperating retaining elements configured for retaining the injection needle at the robot arm, and
wherein the robot arm is configured for lowering the injection needle in a lowering direction to place the injection needle in the needle park station and for subsequently performing a motion in a lateral direction angled relative to the lowering direction to disengage the cooperating retaining elements, thereby disconnecting the injection needle from the robot arm.

16. The sample injector of claim 1, wherein at least a part of the robot arm, the injection needle and the seat is configured to cooperate so that, upon inserting the injection needle into the seat, a locking mechanism is activated for locking the injection needle to the seat and an unlocking mechanism is simultaneously activated for unlocking the injection needle from the robot arm.

17. The sample injector of claim 16, wherein at least one of the locking mechanism or the unlocking mechanism is configured as a mechanism selected from the group consisting of: a mechanical latching mechanism, a mechanical clamping mechanism, and a magnetic mechanism.

18. The sample injector of claim 1, comprising at least one further seat in fluid communication with at least one further fluidic path, wherein the robot arm is configured for accommodating the injection needle selectively in the seat or in at least one of the at least one further seat.

19. The sample injector of claim 18, comprising at least one further needle park station assigned to the at least one further seat and configured for retaining the injection needle when the injection needle is accommodated in a corresponding one of the at least one further seat.

20. The sample injector of claim 18, comprising at least one further injection needle movable by the robot arm, when being connected thereto, between the fluid container containing the fluid and selectively the seat or one of the at least one further seat.

21. The sample injector of claim 1, wherein the robot arm is configured for mounting at least one further tool additionally or alternatively to the injection needle.

22. The sample injector of claim 21, wherein the at least one further tool comprises a tool selected from the group consisting of: a gripper configured for gripping a vial, a reader configured for reading an identification feature of the fluid container or a vial, a filter for filtering the fluid, a pipette tip, a mixer for mixing the fluid, a punching tool for punching a septum covering a fluid container, a plate handling tool configured for handling plates having multiple fluid receptacles, and a combination of two or more of the foregoing.

23. The sample injector of claim 1, wherein the robot arm comprises a stripper tool configured for stripping off a fluid container from the injection needle after having aspirated the fluid from the fluid container.

24. The sample injector of claim 1,
wherein the robot arm is configured for taking out a selected one of a plurality of fluid containers, each containing a fluid, from a fluid container rack and placing the selected fluid container on a fluid container support; and
wherein the robot arm is further configured for moving the injection needle between the selected fluid container placed on the fluid container support containing the fluid and the seat.

25. The sample injector of claim 1,
wherein the robot arm has a first lift mechanism configured for handling a plurality of fluid containers over a first stroke length along a lift axis;
wherein the robot arm has a second lift mechanism configured for handling the injection needle over a second stroke length along the lift axis; and
wherein the first stroke length differs from the second stroke length.

26. A method of injecting a fluid into a fluidic path between a high pressure pump and a separation column, the method comprising:
moving an injection needle connected to a robot arm to a fluid container for aspirating the fluid in the injection needle;
moving the injection needle connected to the robot arm to a seat in fluid communication with the fluidic path, wherein the injection needle forms a part of the fluidic path when accommodated in the seat;
disconnecting the injection needle from the robot arm when the injection needle is accommodated in the seat, such that the injection needle remains a part of the fluidic path after being disconnected from the robot arm;
injecting the aspirated fluid from the injection needle into the fluidic path when the injection needle is accommodated in the seat; and
performing a further task by the robot arm while the injection needle is disconnected from the robot arm.

27. A sample injector for injecting a fluid into a fluidic path between a high pressure pump and a separation column, the sample injector comprising:
a robot arm configured for taking out a selected one of a plurality of fluid containers, each containing a fluid, from a fluid container rack and placing the selected fluid container on a fluid container support,
wherein the robot arm is further configured for moving an injection needle between the selected fluid container placed on the fluid container support containing the fluid and a seat in fluid communication with the fluidic path; and
the injection needle is configured for aspirating the fluid from the fluid container, when the injection needle has been moved to the fluid container, and for injecting aspirated fluid into the fluidic path, when the injection needle is accommodated in the seat, the injection needle forming a part of the fluidic path when accommodated in the seat.

28. The sample injector of claim 27, wherein the fluid container rack comprises a plurality of vertically stacked compartments each configured for accommodating a respective one of the plurality of fluid containers.

29. The sample injector of claim 28, wherein the fluid container rack is operable with a push loading drawer mechanism.

30. The sample injector of claim 27, wherein the robot arm is configured for taking a fluid container from the fluid container support and for moving the fluid container into the fluid container rack.

31. The sample injector of claim 27, wherein at least a part of the plurality of fluid containers is a sample plate comprising a plurality of receptacles each configured for accommodating a fluid.

32. The sample injector of claim 27, wherein the robot arm is configured so that the injection needle is disconnectably mountable on the robot arm and a provision for handling a fluid container of the robot arm is disconnectably mountable or permanently mounted on the robot arm.

33. The sample injector of claim 27, comprising only a single fluid container support configured for receiving exactly one fluid container.

34. The sample injector of claim 27, wherein the robot arm is configured for alternatingly handling the plurality of fluid containers and the injection needle.

35. The sample injector of claim 27,
wherein the robot arm is configured for selectively disconnecting the injection needle from the robot arm when the injection needle is accommodated in the seat; and
wherein the robot arm is configured for handling at least one of the plurality of fluid containers of the fluid container rack while the injection needle is disconnected from the robot arm.

36. The sample injector of claim 27,
wherein the robot arm has a first lift mechanism configured for handling the plurality of fluid containers over a first stroke length along a lift axis;
wherein the robot arm has a second lift mechanism configured for handling the injection needle over a second stroke length along the lift axis; and
wherein the first stroke length differs from the second stroke length.

37. A method of injecting a fluid into a fluidic path between a high pressure pump and a separation column, the method comprising:
taking out a selected one of a plurality of fluid containers, each containing a fluid, from a fluid container rack and placing the selected fluid container on a fluid container support by a robot arm;
aspirating the fluid from the selected fluid container placed on the fluid container support by an injection needle supported by the robot arm;
moving the injection needle to a seat in fluid communication with the fluidic path by the robot arm, the injection needle forming a part of the fluidic path when accommodated in the seat;
disconnecting the injection needle from the robot arm when the injection needle is accommodated in the seat, such that the injection needle remains a part of the fluidic path after being disconnected from the robot arm; and
injecting the aspirated fluid into the fluidic path, when the injection needle is accommodated in the seat.

38. A sample injector for injecting a fluid into a fluidic path between a high pressure pump and a separation column, the sample injector comprising:
a robot arm configured for handling a plurality of fluid containers, each containing a fluid, and for handling an injection needle,
wherein the injection needle is configured for aspirating the fluid from one of the plurality of fluid containers when the injection needle has been moved to the one of the plurality of fluid containers, and for injecting the aspirated fluid into the fluidic path when the injection needle is accommodated in a seat in fluid communication with the fluidic path, the injection needle forming a part of the fluidic path when accommodated in the seat;
wherein the robot arm comprises a first lift mechanism configured for handling the plurality of fluid containers over a first stroke length along a lift axis;
wherein the robot arm comprises a second lift mechanism configured for handling the injection needle over a second stroke length along the lift axis;
wherein the first stroke length differs from the second stroke length; and
wherein the robot arm is configured for selectively disconnecting the injection needle from the robot arm when the injection needle is accommodated in the seat, such that the injection needle remains a part of the fluidic path after being disconnected from the robot arm.

39. The sample injector of claim 38, wherein the first stroke length is larger than the second stroke length.

40. The sample injector of claim 38, wherein the robot arm is movable by a horizontal drive mechanism in a plane perpendicular to the lift axis.

41. The sample injector of claim 38, wherein the lift axis is a vertical axis.

42. The sample injector of claim 38, wherein the first lift mechanism and the second lift mechanism are operable independently from one another.

43. The sample injector of claim 38, wherein the robot arm is configured for handling at least one of the plurality of fluid containers of the fluid container rack while the injection needle is disconnected from the robot arm.

44. The sample injector of claim 38, wherein the robot arm is configured for taking out a selected one of the plurality of fluid containers from the fluid container rack and placing the selected fluid container on a fluid container support by using the first lift mechanism.

45. The sample injector of claim 44, wherein the robot arm is configured for moving the injection needle between the selected fluid container placed on the fluid container support containing the fluid and the seat by using the second lift mechanism.

46. A method of injecting a fluid into a fluidic path between a high pressure pump and a separation column, the method comprising:
 handling a selected one of a plurality of fluid containers, each containing a fluid, by actuating a first lift mechanism of a robot arm operable over a first stroke length along a lift axis;
 handling an injection needle, for aspirating the fluid from one of the plurality of fluid containers and for injecting the aspirated fluid into the fluidic path, by actuating a second lift mechanism of the robot arm operable over a second stroke length along the lift axis,
 wherein the first stroke length differs from the second stroke length;
 moving the injection needle to a seat in fluid communication with the fluidic path by the robot arm, the injection needle forming a part of the fluidic path when accommodated in the seat; and
 disconnecting the injection needle from the robot arm when the injection needle is accommodated in the seat, such that the injection needle remains a part of the fluidic path after being disconnected from the robot arm.

47. A fluid separation system for separating compounds of a fluid in a mobile phase, the fluid separation system comprising:
 a mobile phase drive configured to drive the mobile phase through the fluid separation system,
 a separation unit configured for separating compounds of the fluid in the mobile phase, and
 a sample injector according to claim 1 configured for injecting the fluid in the fluidic path between the mobile phase drive and the separation unit.

48. The fluid separation system according to claim 47, comprising at least one of the following features:
 the fluid separation system is configured to analyze at least one physical, chemical and/or biological parameter of at least one compound of the fluid;
 the fluid separation system comprises at least one of the group consisting of a detector device, a device for chemical, biological and/or pharmaceutical analysis, a capillary electrophoresis device, a liquid chromatography device, an HPLC device, a gas chromatography device, a gel electrophoresis device, and a mass spectroscopy device;
 the fluid separation system is configured to conduct the fluid with a high pressure;
 the fluid separation system is configured to conduct the fluid with a pressure of at least 100 bar;
 the fluid separation system is configured as a microfluidic device;
 the fluid separation system is configured as a nanofluidic device;
 the separation unit is configured for retaining a part of components of the fluid and for allowing other components of a mobile phase to pass the separation unit;
 at least a part of the separation unit is filled with a separating material;
 at least a part of the separation unit is filled with a separating material, wherein the separating material comprises beads having a size in the range of 1 μm to 50 μm;
 at least a part of the separation unit is filled with a separating material, wherein the separating material comprises beads having pores having a size in the range of 0.01 μm to 0.2 μm.

* * * * *